(12) United States Patent
Wheeler

(10) Patent No.: US 11,160,696 B2
(45) Date of Patent: Nov. 2, 2021

(54) LIQUID AND SOLID POROUS-ABSORBENT ARTICLE

(71) Applicant: Clarence Wheeler, Atlanta, GA (US)

(72) Inventor: Clarence Wheeler, Atlanta, GA (US)

(*) Notice: Subject to any disclaimer, the term of this patent is extended or adjusted under 35 U.S.C. 154(b) by 398 days.

(21) Appl. No.: 16/350,417

(22) Filed: Mar. 14, 2019

(65) Prior Publication Data
US 2019/0209399 A1 Jul. 11, 2019

Related U.S. Application Data

(63) Continuation-in-part of application No. 15/438,318, filed on Feb. 21, 2017, now abandoned.

(51) Int. Cl.
| | | |
|---|---|---|
| A61F 13/505 | (2006.01) | |
| A61F 13/534 | (2006.01) | |
| A61G 9/00 | (2006.01) | |
| A61G 17/06 | (2006.01) | |
| A47K 11/04 | (2006.01) | |
| A47K 17/00 | (2006.01) | |
| A61F 13/49 | (2006.01) | |
| A61F 13/45 | (2006.01) | |
| A61F 13/53 | (2006.01) | |
| A61G 17/007 | (2006.01) | |

(52) U.S. Cl.
CPC ............ *A61F 13/534* (2013.01); *A47K 17/00* (2013.01); *A61F 13/49009* (2013.01); *A61F 13/505* (2013.01); *A61G 9/003* (2013.01); *A47K 11/04* (2013.01); *A61F 2013/4587* (2013.01); *A61F 2013/5307* (2013.01); *A61F 2013/53035* (2013.01); *A61F 2013/530131* (2013.01); *A61F 2013/530489* (2013.01); *A61F 2013/530591* (2013.01); *A61G 17/0106* (2017.05); *A61G 17/06* (2013.01)

(58) Field of Classification Search
CPC ....... A47K 11/04; A47K 17/00; A61F 13/505; A61F 13/534; A61F 13/49009; A61F 2013/4587; A61F 2013/5307; A61F 2013/53035; A61F 2013/530131; A61F 2013/530489; A61F 2013/530591; A61G 9/003; A61G 17/06; A61G 17/0106
USPC ............................................................. 4/484
See application file for complete search history.

(56) References Cited

U.S. PATENT DOCUMENTS 3,471,871 A * 10/1969 Nociti ....................... A61F 5/44
4/484
3,885,568 A * 5/1975 Schaar .............. A61F 13/00021
604/366

(Continued)

*Primary Examiner* — Joshua E Rodden

(57) ABSTRACT

The present invention discloses an absorbent article for attachment to the interior of a child potty/bed pan or to be worn on an user. The absorbent article composes an absorbent core, first absorbent channel layer, intermediate channel layer and top permeable layer composes made up of permeable materials and further includes a material capable of converting a liquid substance to a gel-like substance. Specifically, regions of the absorbent core first absorbent channel layer and intermediate channel layer may include a super absorbent polymer (SAP) material such as hydrogel, sodium polyacrylate, polyacrylate absorbents, or a biodegradable material such as a powder corn starch or wheat mixture or a combination of super absorbent polymer (SAP) and a biodegradable material.

15 Claims, 19 Drawing Sheets

(56) References Cited

U.S. PATENT DOCUMENTS

| | | | | |
|---|---|---|---|---|
| 4,227,531 A * | 10/1980 | McLeod | A61F 13/472 | 2/406 |
| 4,979,833 A * | 12/1990 | Cook | A45C 3/00 | 383/109 |
| 5,188,627 A * | 2/1993 | Igaue | A61F 13/49 | 604/358 |
| 5,669,896 A * | 9/1997 | Kielpikowski | A61F 13/49009 | 604/373 |
| 5,833,678 A * | 11/1998 | Ashton | A61F 13/534 | 604/378 |
| 5,866,242 A * | 2/1999 | Tan | D04H 1/732 | 428/219 |
| 6,056,732 A * | 5/2000 | Fujioka | A61F 13/49009 | 604/385.01 |
| 6,070,277 A * | 6/2000 | Thomas | A47K 11/06 | 4/484 |
| 6,115,855 A * | 9/2000 | Lorenzo | A47K 11/105 | 4/484 |
| 2002/0091368 A1* | 7/2002 | LaVon | A61F 13/505 | 604/385.14 |
| 2002/0111596 A1* | 8/2002 | Fletcher | A61F 13/565 | 604/385.03 |
| 2002/0123729 A1* | 9/2002 | Bewick-Sonntag | A61F 13/5376 | 604/378 |
| 2002/0173762 A1* | 11/2002 | Ishikawa | A61F 13/538 | 604/385.01 |
| 2003/0135179 A1* | 7/2003 | Krautkramer | A61F 13/534 | 604/370 |
| 2006/0080767 A1* | 4/2006 | Dombe-Korody | A47K 11/06 | 4/484 |
| 2006/0080768 A1* | 4/2006 | Smith, Jr. | A47K 11/04 | 4/484 |
| 2007/0163038 A1* | 7/2007 | Sharp | A47K 11/06 | 4/484 |
| 2007/0271691 A1* | 11/2007 | Cortez | A47K 11/06 | 4/484 |
| 2009/0043273 A1* | 2/2009 | Carlucci | A61F 13/534 | 604/370 |
| 2009/0246447 A1* | 10/2009 | Luo | B32B 3/02 | 428/78 |
| 2009/0255046 A1* | 10/2009 | Carter | A47K 11/06 | 4/484 |
| 2012/0222208 A1* | 9/2012 | Jacobson | A61F 5/4556 | 4/484 |
| 2013/0086737 A1* | 4/2013 | Bizar | A47K 11/02 | 4/484 |
| 2013/0191971 A1* | 8/2013 | Collins | A61F 13/5605 | 2/400 |
| 2013/0211358 A1* | 8/2013 | Kikkawa | A61F 13/53708 | 604/367 |
| 2015/0173977 A1* | 6/2015 | Stelzig | A61F 13/53 | 604/378 |
| 2015/0313770 A1* | 11/2015 | Hubbard, Jr. | A61F 13/534 | 604/369 |
| 2016/0045086 A1* | 2/2016 | Arroyo | A47K 13/06 | 4/484 |
| 2016/0100989 A1* | 4/2016 | Seitz | A61F 13/49011 | 604/374 |
| 2016/0100999 A1* | 4/2016 | Hamilton | A61F 13/4963 | 604/372 |
| 2017/0021051 A1* | 1/2017 | Richards | A61F 13/5633 | |
| 2017/0065134 A1* | 3/2017 | Tanguay | A47K 11/02 | |
| 2017/0065460 A1* | 3/2017 | Rosati | A61F 13/51104 | |
| 2017/0119597 A1* | 5/2017 | Bewick-Sonntag | A61F 13/534 | |
| 2017/0135867 A1* | 5/2017 | Hashimoto | A61F 13/4902 | |
| 2017/0216111 A1* | 8/2017 | Kleuskens | A61F 13/5616 | |
| 2017/0238772 A1* | 8/2017 | Wheeler | A47K 11/105 | |
| 2017/0239107 A1* | 8/2017 | Castrogiovanni | A61F 13/49413 | |
| 2017/0281422 A1* | 10/2017 | Herfert | B32B 37/1284 | |
| 2018/0008485 A1* | 1/2018 | Ehrnsperger | A61F 13/5323 | |
| 2019/0083325 A1* | 3/2019 | McCormick | A61F 13/51121 | |
| 2019/0159945 A1* | 5/2019 | Tokunaga | A61F 13/532 | |
| 2019/0209399 A1* | 7/2019 | Wheeler | A47K 17/00 | |
| 2019/0307617 A1* | 10/2019 | Joshi | A61F 13/53 | |
| 2020/0170853 A1* | 6/2020 | Brennan | A61F 13/496 | |
| 2020/0179187 A1* | 6/2020 | Tagomori | A61F 13/53752 | |
| 2020/0188191 A1* | 6/2020 | Kuramochi | A61F 13/4704 | |
| 2020/0237581 A1* | 7/2020 | Chmielewski | A61F 13/534 | |
| 2020/0315863 A1* | 10/2020 | Kuo | A61F 13/505 | |
| 2021/0093489 A1* | 4/2021 | Manabe | A61F 13/534 | |
| 2021/0100695 A1* | 4/2021 | Ishibashi | A61F 13/49012 | |

\* cited by examiner

ELEMENT ADDED 1.

LIQUID AND SOLID POROUS-ABSORBENT ARTICLE

BACKGROUND OF THE INVENTION

Field of the Invention

This invention relates to the field of an personal hygiene article configured to absorb an liquid and solid substance.

BRIEF SUMMARY OF THE INVENTION

The invention comprises an absorbent article, for example the absorbent article can be and not limited to an liner used in conjunction with an child potty training unit or an adults bed pan, an child diaper, an adult diaper, or an feminine hygiene liner. Further, the absorbent article consist of liquid permeable layers and non-permeable layers. In addition the layers can compose and form from an absorbent fibrous material of cotton or wood pulp or cotton or wood fluff. Further, the absorbent article may comprise an super absorbent polymer (SAP) material such as hydrogel, sodium polyacrylate, polyacrylate absorbents, or an biodegradable material such as an powder corn starch or wheat mixture or an combination of super absorbent polymer (SAP) and an biodegradable material. The absorbent article may comprises of an outer base, absorbent core, intermediate absorbent layer, and top sheet. Further, the layers of the absorbent article may be formed by process of meshing an absorbent material together such as cotton or wood pulp of fluff to form an permeable layer. The outer base as non-permeable layer may be formed by combining multiple micro-film layers together by process of lamination or any other method known to one skilled in the art(s).

The upside of the present invention overcomes the shortcomings of the prior art by providing an absorbent article which is easy to use cheap to manufacture and teaches an more advance configuration of the said absorbent article.

BRIEF DESCRIPTION OF SEVERAL VIEWS OF THE DRAWINGS

These and other features and advantages of the present invention will be readily appreciated as the same becomes better understood by reference to the following detailed description when considered in connection with accompanying drawings, wherein.

DETAILED DESCRIPTION OF THE INVENTION

Referring to the figures wherein like numerals indicated like or corresponding features throughout the view, an exemplary disposable liner is generally shown at 1 and absorbent article at 40 for purpose of illustration and not to be in any way limiting. Further, in the figures the broken/dashed lines represents the separation of components in conjunction with another component according to the embodiment(s).

Figure 1A:
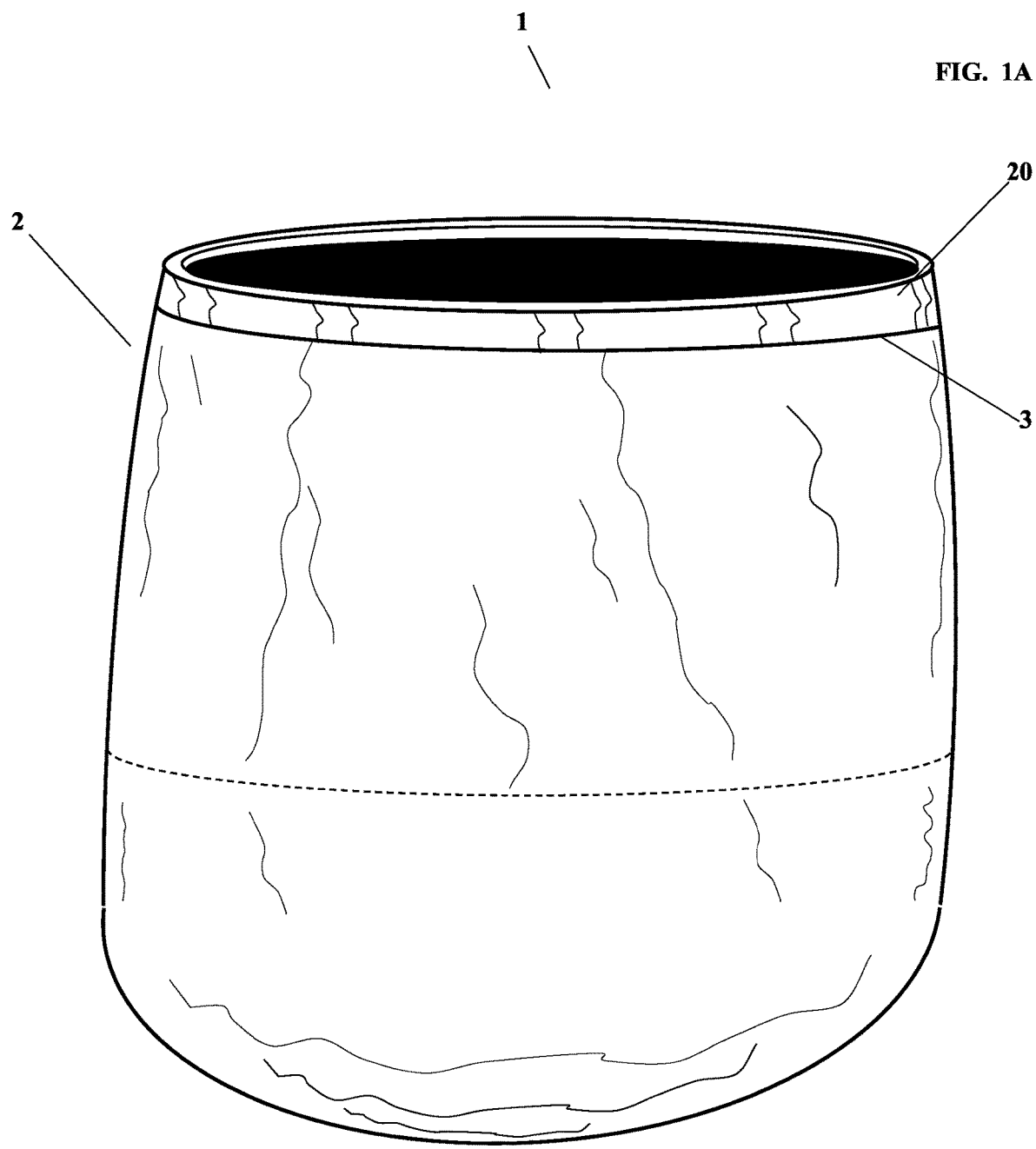
FIG. 1A-1E is a perspective view of an layer structuring of an potty/bed pan liner article according to one embodiment.
Figure 1B:
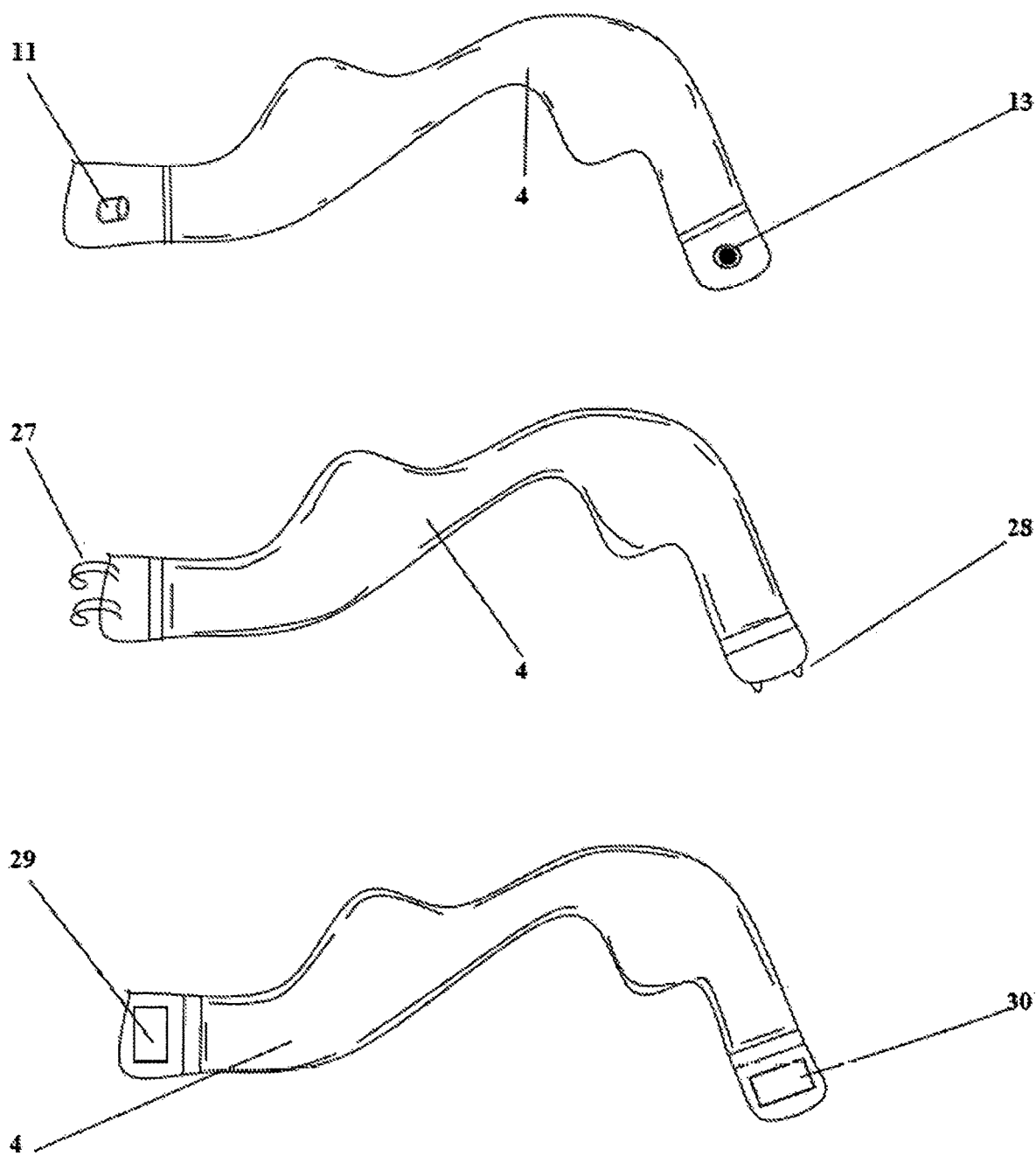
Figure 1C:
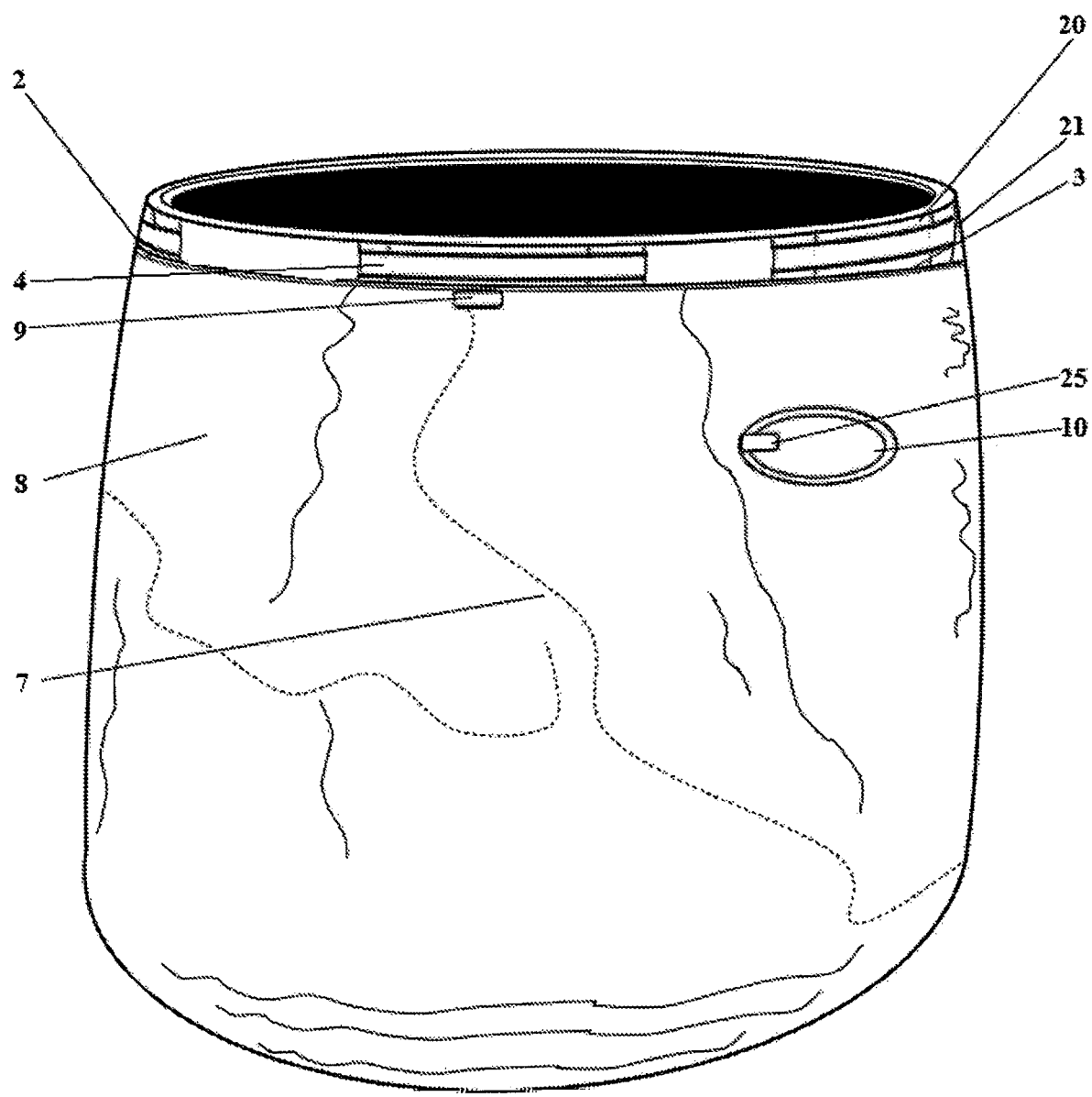

FIG. 1A-1C is a perspective view of an layering structure of the liner 1. The liner 1 composes of an bowl shape first non-permeable layer 2 and second non-permeable layer 8. The first non-permeable layer 2 is made of an impermeable plastic material further forming the overall foundation of the said liner 1. The top portion of the first non-permeable layer 2 composes an elastic rim member 3 configured to allow the top portion of the liner 1 to grip and assemble around the rim of potty FIG. 1A. The elastic material 4 assembles approximately 25.4 mm beneath the top edge of first non-permeable layer 2 leaving approximately 38.1 mm of first non-permeable layer 2 at an area above top edges of the elastic material 4, the remaining top portion of first non-permeable layer 2 is folded/cuffed inward in direction behind elastic material 4 and further stitched or coupled together by an appropriate adhesive forming an elastic rim member 3. In addition the first non-permeable layer 2 composes a respectively dashed slit 31 formed around its surface arranged at a circular (ring) direction approximately 38.1 mm to 76.2 mm above its base region, whereas the first non-permeable layer 2 dashed slit 31 respectively corresponds with the preceding absorbent core 16 dashed slit 31, first absorbent channel layer 12 dashed slit 31, intermediate absorbent channel layer 18 dashed slit 31, and top permeable layer 22 dashed slit 31 which allocates an user to bifurcate the entire lower region of the first non-permeable layer 2 and preceding absorbent core 16, first absorbent channel layer 12, intermediate absorbent channel layer 18 and top permeable layer 22 below the dashed slit(s) 31.

Alternatively, the first non-permeable layer 2 composes an elastic placement portion 20, where approximately 31.75 mm to 38.01 mm of the top portion of the first non-permeable layer 2 is respectively folded/cuffed inward in an direction towards the interior region of first non-permeable layer 2, furthermore the top portion is stitched or bonded to an interior region by an adhesive forming the elastic placement portion 20, in conjunction the elastic placement portion 20 walls composes an partial spacing in between configured to allocate the elastic material 4 to assemble an arrange within. Additionally, the elastic placement portion 20 comprises a plurality of slits 21 approximately 38.1 mm to 63.05 apart from each and approximately 12.07 mm to 19.05 mm in length vertically. The elastic material 4 is introduced into the slit 21 and into a corresponding slit 21 by a weaving process, further regions of the elastic material 4 are subjected outside of the elastic placement portion 20 in-between every other corresponding slit 21. Further, elastic material 4 portion that is subjected outside of the elastic placement portion 20 displays a emblem such as a cartoon character, alphabet, animal, or company logo.

More of, the elastic material 4 composes a respective button 11 and a respective button hole 13. Where when both ends of the elastic material 4 respectively convene at the front region of the elastic placement portion 20 it forms an button coupling method. Alternatively, the elastic material 4 composes a pair of hook(s) 27 and a hook loop 28. Where when both ends of elastic material 4 respectively convene at the front region of elastic placement portion 20 it form an hook coupling method. Instead, the elastic material 4 composes a velcro strip 29 and a velcro mate 30. Where when both ends of elastic material 4 respectively convene at the front region of elastic placement portion 20 it form an velcro coupling method FIG. 1B The liner 1 further composes an bowl shape second non-permeable layer 8 coupled to the exterior of the first non-permeable layer 2 comprising an body reedier than the overall body of the first non-permeable layer 2 made of an impermeable plastic material assembling directly below the elastic rim member 5 of the first non-permeable layer 8. Alternatively, the second non-permeable layer 8 can be coupled to the exterior region of the first non-permeable layer 2 by an lamination method without the intervening of an additional element. The second non-permeable layer 8 composes a dashed swirled slit 7 originating at a bottom edge of the tab 9, in contrast the dashed swirled slit 7 arranges around the entire body of the second non-permeable layer 8 ending at a region slightly adjacent where the dashed swirled slit 7 originates. When the tab 9 is pulled at a complete clock-wise or circular direction around the second non-permeable layer 8 the entire second non-permeable layer 8 is bifurcated from the first non-permeable layer 2 respectively.

Further, the second non-permeable layer 8 includes a tab 9 affixed at a top edge region of the second non-permeable layer 8 exterior envisioned to allocate a user to bifurcate the entire second non-permeable layer 8 from the first non-permeable layer 2. Specifically, the tab 9 is approximately 6.35 to 19.05 mm in longitude and approximately 6.35 mm to 12.07 mm in latitude according to dimensions.

Additionally, the second non-permeable layer 8 includes a adhesive tab 10 affixed at a mid-range region of the second non-permeable layer 8, comprising an flanged tip 25 affixed at a edge region of the adhesive tab 10, further the adhesive tab 10 conceals the handle hole 5 on the second non-permeable layer 8 whereas when the adhesive tab 10 is removed (peeled) from second non-permeable layer 8 this allocates the potty handle to deviate the hole 5 from the interior of the second non-permeable layer 8 FIG. 1C. More on the adhesive tab 10 is elliptical-shape. Further an double-side tape is respectively coupled to the second non-permeable layer 8 boarding the hole 5 edges where the adhesive tab 10 assembles on top of the hole 5 further the interior edges of the adhesive tab 10 obtains a region of the double-sided tape. Instead, the adhesive tab 10 can be made of an plastic material composing of an adhesive or double-sided tape at the rear region coupling the adhesive tab 10 to second non-permeable layer 8.

Figure 1D:
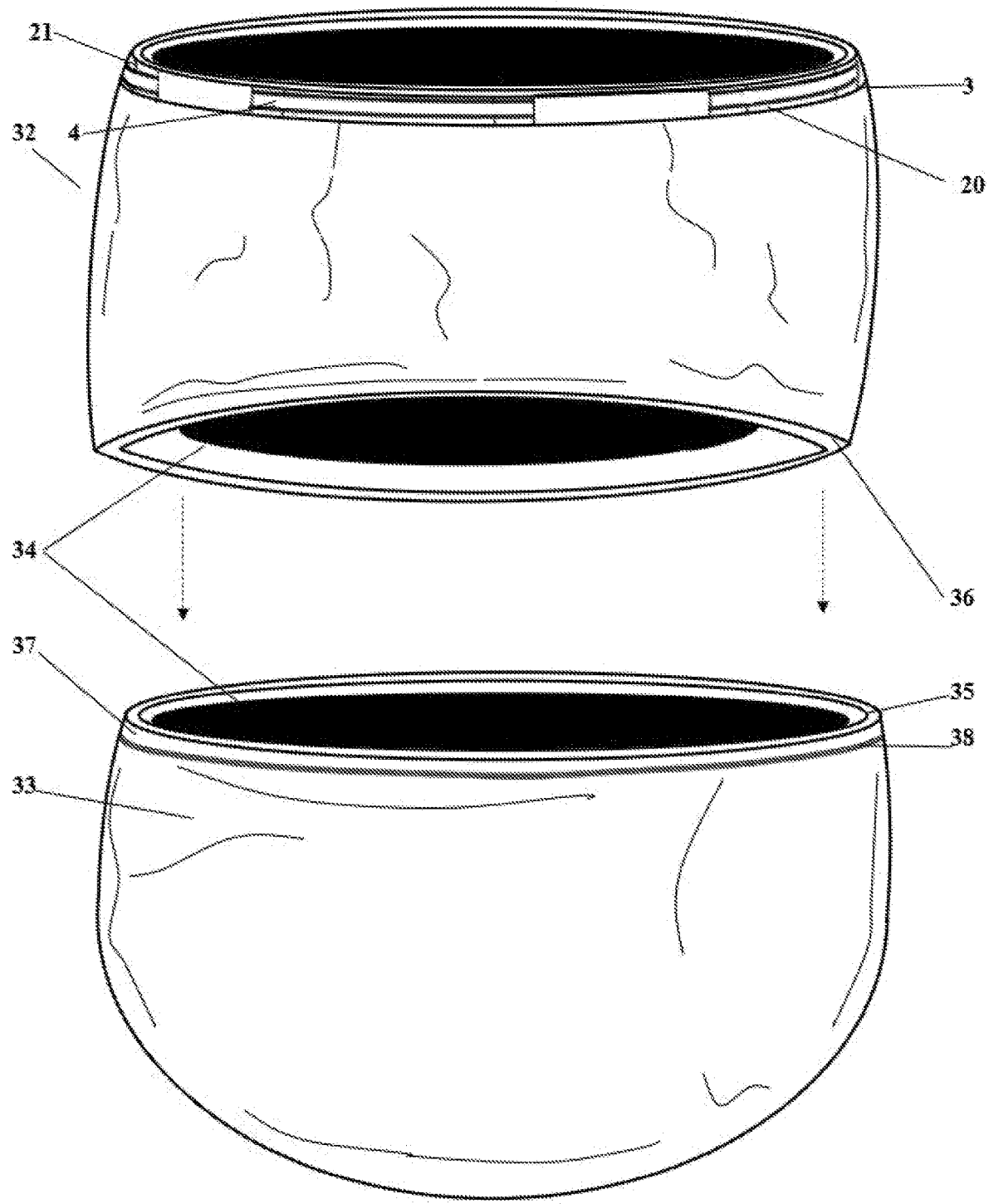
Figure 1E:
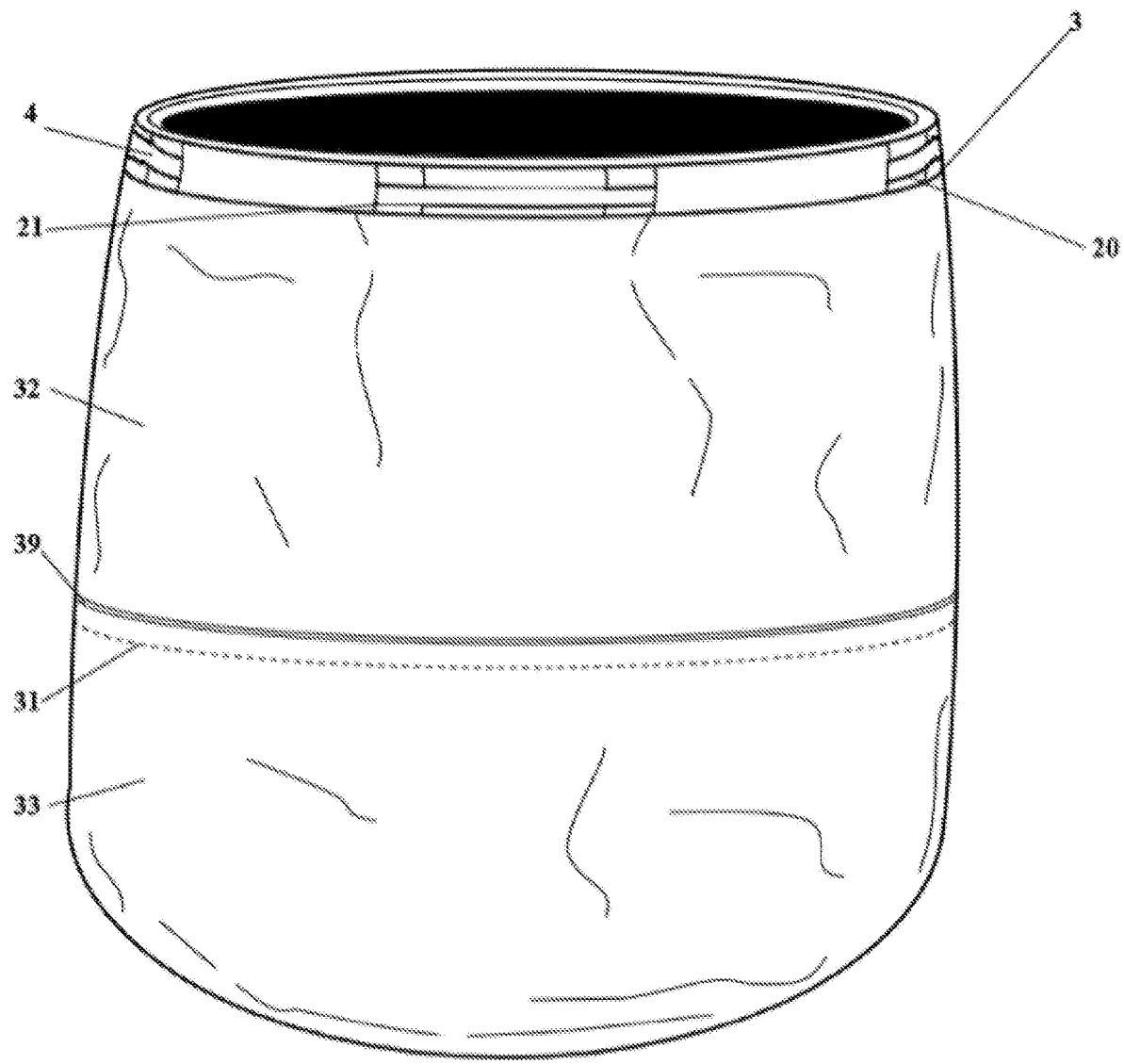

Signifying FIGS. 1D & 1E, alternatively the first non-permeable layer 2 forms an bowl shape composing an first portion 32 and second portion 33. More specifically, the first portion 32 refers to the top half of the liner 1 and the second portion 33 refers to the lower half of the liner 1. The first portion 32 forms an partial bowl shape arranging parallel sides composing an opening 34 at the lower region. Further, the top region of the first portion 32 composes an elastic rim member 3 configured to allow the top portion of the liner 1 to grip and assemble around the rim of potty. More of, the elastic rim member 3 composes an elastic placement portion 20 configured to allocate the elastic material 4 to assemble therein forming the overall structure of the elastic rim member 3 as mention in FIG. 1A. The first portion 32 is made of a impermeable plastic material.

In general, the second portion 33 forms an half-moon shape with parallel side composing a opening 34 at the top region. More, the second portion 33 composes a adhesive strip 37 arranged around the top edges 35 approximately 6.35 mm in width.

The bottom edges 38 of the adhesive strip 37 respectively receives the bottom edges 36 of the first portion 32 respectively joining the first portion 32 to the second portion 33. The second portion 33 is made of a liquid-soluble film made of a polyvinylalcohol (PVA) material.

In addition, the second portion 33 composes a dashed slit 31 arranged at a circular (ring) direction approximately 6.35 mm below the joining region 39 of the first portion 32 and second portion 33. The dashed slit 31 respectively corresponds with the preceding absorbent core 16 dashed slit 31, first absorbent channel layer 12 dashed slit 31, intermediate absorbent channel layer 18 dashed slit 31 and top permeable layer 22 dashed slit 31 which allocates a user to bifurcate the entire lower region of the liner 1 accompanying the first non-permeable layer 25, absorbent core 16, first absorbent channel layer 12, intermediate absorbent channel layer 18 and top permeable layer 22 below the dashed slit(s) 31. Alternatively, the liner 1 of FIGS. 1D & 1E can comprises an second non-preamble layer 8 and other components an mentioned above with reference to FIGS. 1A-1C.

FIG. 2A-2E. is a perspective view of an layer structuring of the liner 1. Further, the inner portion of liner 1 composes an bowl shape absorbent core layer 16 coupled to the interior of the first non-permeable layer 2, forming the body of an sack/pouch with reedy density walls, comprising an extending portion that completely boarders the top edges of the sack/pouch portion 24 extending upwardly in direction approximately 12.07 mm to 25.04 mm in length forming the flange bordering 23, where the flanged boarding 23 is affixed right below the first non-permeable layer 2 elastic rim member 3 FIG. 2A.

Moreover, the absorbent core 16 is impregnated with a combination of a loose absorbent fibrous matrix, a plurality of super absorbent pods impregnated with loose fine particles of super absorbent polymer (SAP), and loose fine particles of super absorbent polymer (SAP) capable of converting the absorbent core 16 from a dry permeable texture to a moist gel-like permeable texture when in contact with a liquid substance.

Specifically, the super absorbent pods are water-soluble pouches made of an polyvinylalcohol (PVA) film or a derivative of PVA, and alternatively can be cast from other water-soluble materials such as polyethylene oxide or methyl cellulose or other components known to one skilled in the art(s). The super absorbent pods can be of any configuration but preferably according to the arrangement of the super absorbent pods in conjunction with the absorbent article 40 the pods composes a quadrilateral-shape, spherical-shape, or an elliptical-shape.

The super absorbent pods comprise a water/liquid-soluble outer core impregnated with loose fine particles of super absorbent polymer (SAP) or loose fine particles of biodegradable material such as corn starch or wheat, alternative the super absorbent pods contains a combination mixture of loose fine particles of super absorbent polymer (SAP) and loose absorbent fibrous matrix of cotton or wood pulp or cotton or wood fluff. The super absorbent polymer (SAP), biodegradable material, and loose absorbent fibrous matrix may be dispersed through the super absorbent pods at the time the super absorbent pods is created or by any means available to those skilled in the art(s). The super absorbent pods can form any size or shape.

The super absorbent pods performs identical to laundry and dishwasher detergent pods when in contact with water or an liquid substance, the water-soluble films are made by companies like MonoSol located at 707 E. 80$^{th}$ Place Suite 301 Merrillville, Ind. 46410, United States 1-800-237-9552. Watersol located at Arrow Greentech Ltd., Solitaire Corporate Park, Bldg No 3, 7$^{th}$ Floor, Unit No 372, Guru Hargovindji Marg, Chakala, Andheri (East), Mumbai 400093, Phone (+91)-(022) 4074-9000. Coatings Pro Magazine located at 4501 Mission Bay Dr., Suite 2G, San Diego, Calif. 92109, United States 1-858-768-0825.

More specifically, the absorbent core 16 contains a combination of loose absorbent fibrous matrix dispersed respectively throughout the bottom of the absorbent core 16 sack/pouch portion 24, a plurality of super absorbent pods dispersed respectively above the loose absorbent fibrous matrix, and loose fine particles of super absorbent polymer (SAP) dispersed respectively above engulfing the super absorbent pods. The absorbent core 16 sack/pouch portion 24 component capacity ratio is approximately 10% to 20% of loose absorbent fibrous matrix 52 of cotton fluff pulp, approximately 20% to 30% of super absorbent pods 51, wherein the super absorbent pods 51 are respectively impregnated with super absorbent polymer (SAP) in the form of fine particles of sodium polyacrylate at 75% and hydrophilic polymer at 25%, and approximately 40% to 60% of loose fine particles of super absorbent polymer (SAP) 53 in the form of fine particles of sodium polyacrylate 55 at 75% and hydrophilic polymer 56 at 25% FIG. 2B.

The super absorbent pods 51 impregnated into the absorbent core 16 sack/pouch portion 24 are approximately 5 mm to 8 mm in overall spherical circumference, composing a 100% ratio of super absorbent polymer (SAP). The loose absorbent fibrous matrix, super absorbent pods, and loose fine particles of super absorbent polymer (SAP) may be dispersed through the absorbent core 16 sack/pouch portion 24 at the time the absorbent core 16 is created, or by any means available to those skilled in the art(s). Further, the interior walls of the sack/pouch portion 24 composes an light coating of adhesive to retain some of the absorbent fibrous matrix and fine particles of super absorbent polymer (SAP) in place and to ensure evenly distribution of coverage.

The absorbent core 16 composes a respectively dashed slit 31 arranged around its surface arranged at a circular (ring) direction approximately 38.1 mm to 76.2 mm above its base region, further the absorbent core 16 dashed slit 31 respectively corresponds with the preceding first non-permeable layer 2 dashed slit 31, first absorbent channel layer 12 dashed slit 31, intermediate absorbent channel layer 18 dashed slit 31 and top permeable layer 22 dashed slit 31 which allocates the entire lower region of the absorbent core 16 below the dashed slit 31 to bifurcate with the preceding lower region of the first non-permeable layer 2, first absorbent channel layer 12, intermediate absorbent channel layer 18 and top permeable layer 22.

Further, the inner portion of the liner 1 composes a bowl shape first absorbent channel layer 12 coupled to the exterior of the absorbent core 16, where the top edges of the first absorbent channel layer 12 assembles approximately 6.03 mm to 12.52 mm below absorbent core 16 flange boarding 23 top edges thereon adjoining first absorbent channel layer 12 to the absorbent core 16. More to, the first absorbent channel layer 12 composes a respectively dashed slit 31 arranged around its surface arranged at a circular (ring) direction approximately 38.1 mm to 76.2 mm above its base region, the first absorbent channel layer 12 dashed slit 31 arranges at a recessed region above or below at lease one absorbent channel 17, further the dashed slit 31 respectively corresponds with the preceding first non-permeable layer 2 dashed slit 31, absorbent core 16 dashed slit 31, intermediate absorbent channel layer 18 dashed slit 31, and top permeable layer 22 dashed slit 31 which allocates the entire lower region of the first absorbent channel layer 12 below the dashed slit 31 to bifurcate with the preceding lower region of the first non-permeable layer 2, absorbent core 16, intermediate absorbent channel layer 18 and top permeable layer 22.

Further, the first absorbent channel layer 12 forms a reedy permeable sheet where numerous regions of the structure forms effervesce circular shaped pockets that extends profusely in a direction away from the body of the first absorbent channel layer 12. The absorbent channels 17 direct around the entire region of the absorbent channel layer 12 at a horizontal ring (circular) direction approximately 12.07 mm to 25.04 mm apart from each-other. The absorbent channels 17 pattern covers a partial region of the first absorbent channel layer 12 where the opposing regions are recessed FIG. 2C.

The absorbent channels 17 of the first absorbent channel layer 12 can be formed by applying an direct or indirect heat to allocate flexibility of the absorbent channel layer 12 in conjunction with an shape-forming molding press compression machine to mold the desired pattern or any other shape-forming method used by an manufacture known to one skilled in the art(s).

Proceeding, the first absorbent channel layer 12 channel openings 19 is impregnated with a combination of materials capable of maintaining the shape and pattern structure of the absorbent channels 17 and converting the absorbent channels 17 region from a dry permeable texture to a gel-like permeable texture when in contact with a liquid substance. Specifically, the first absorbent channel layer 12 absorbent channels 17 contains a combination of loose absorbent fibrous matrix dispersed respectively throughout the bottom region of the channel openings 19, super absorbent pods respectively arranged above the loose absorbent fibrous matrix at each absorbent channel 17, and loose fine particles of super absorbent polymer (SAP) dispersed respectively above engulfing the super absorbent pod.

Figure 2A:
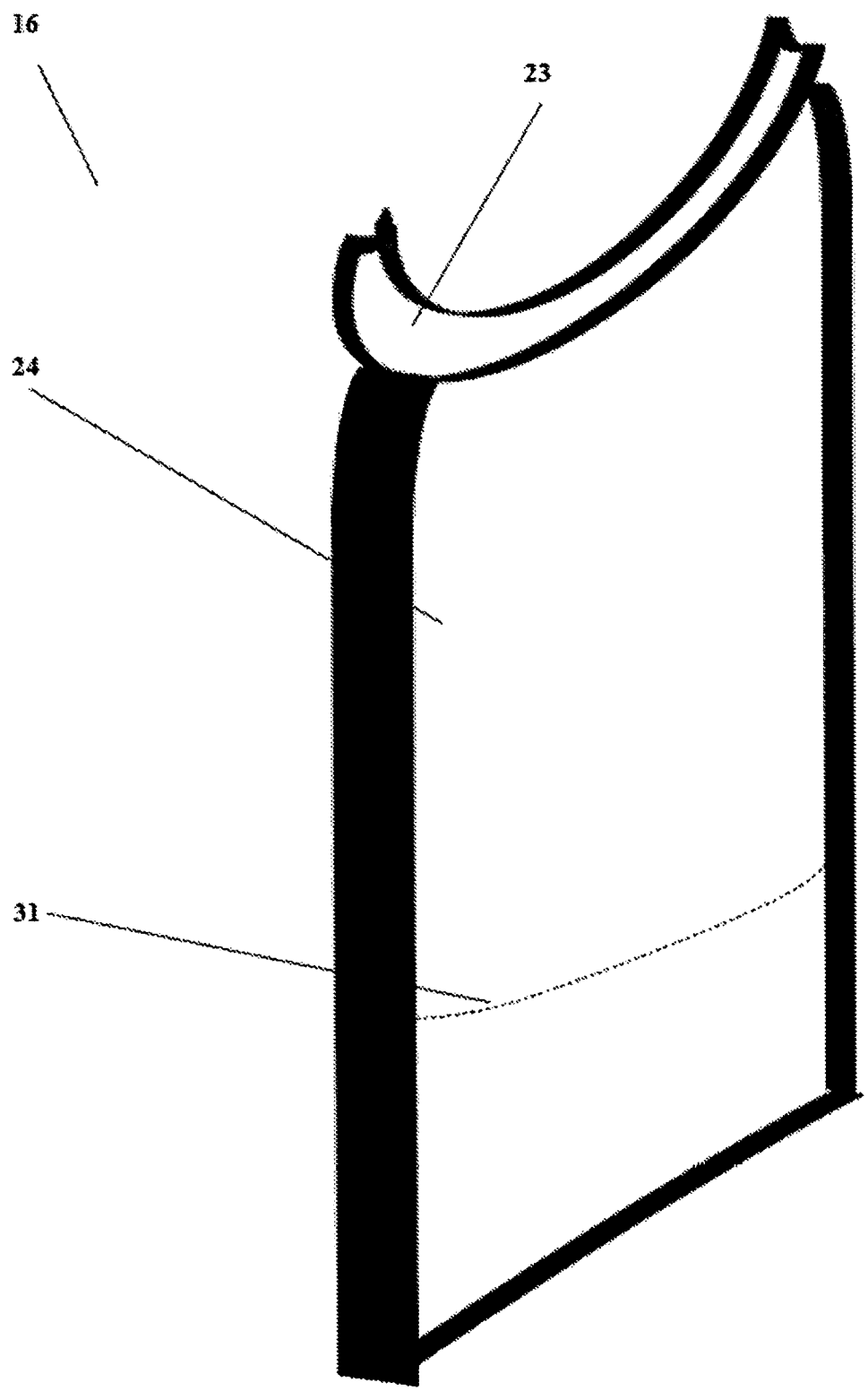
FIG. 2A-2E is a perspective view of an layer structuring of an potty/bed pan liner article according to another embodiment.
Figure 2B:
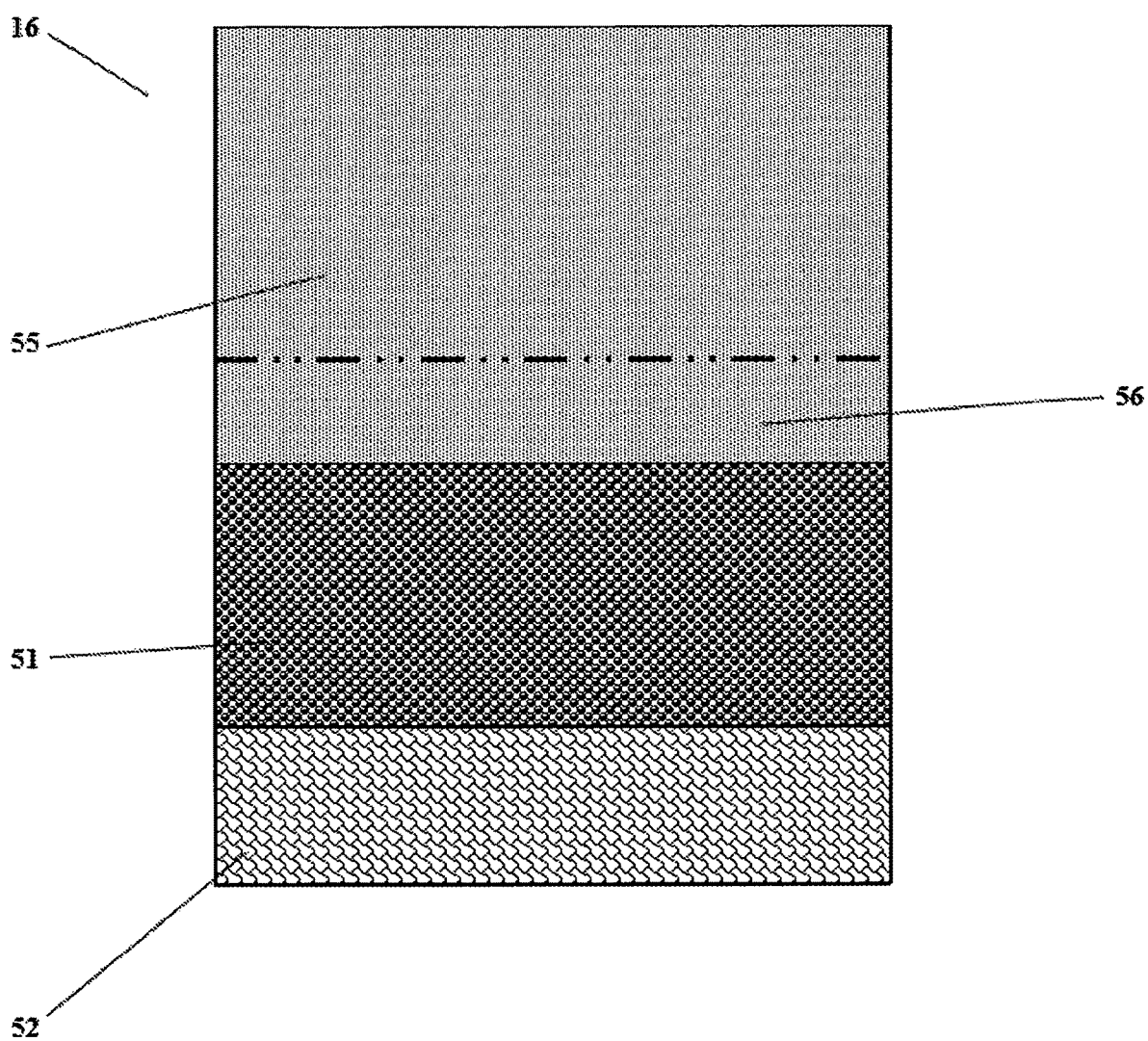
Figure 2C:
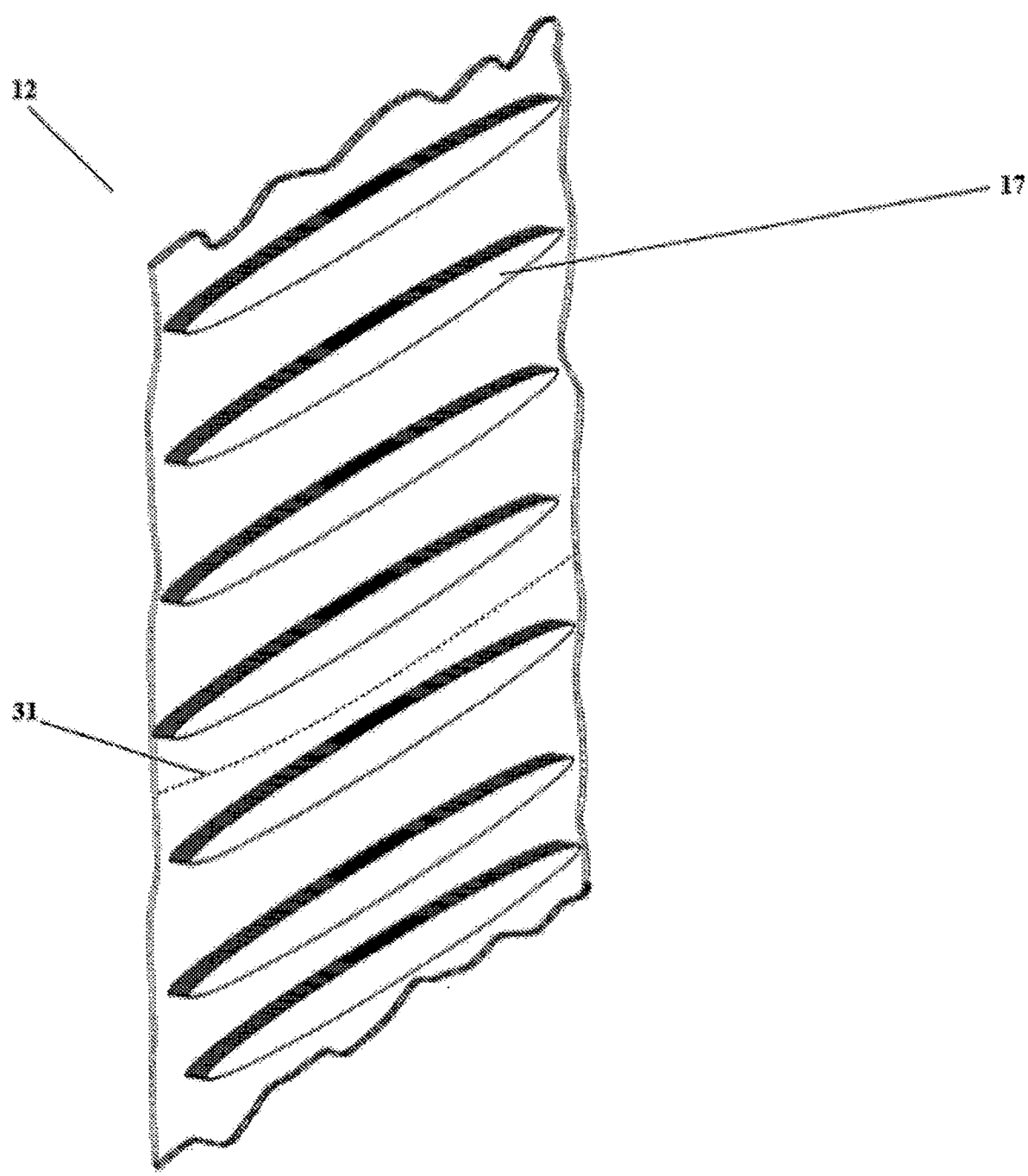
Figure 2D:
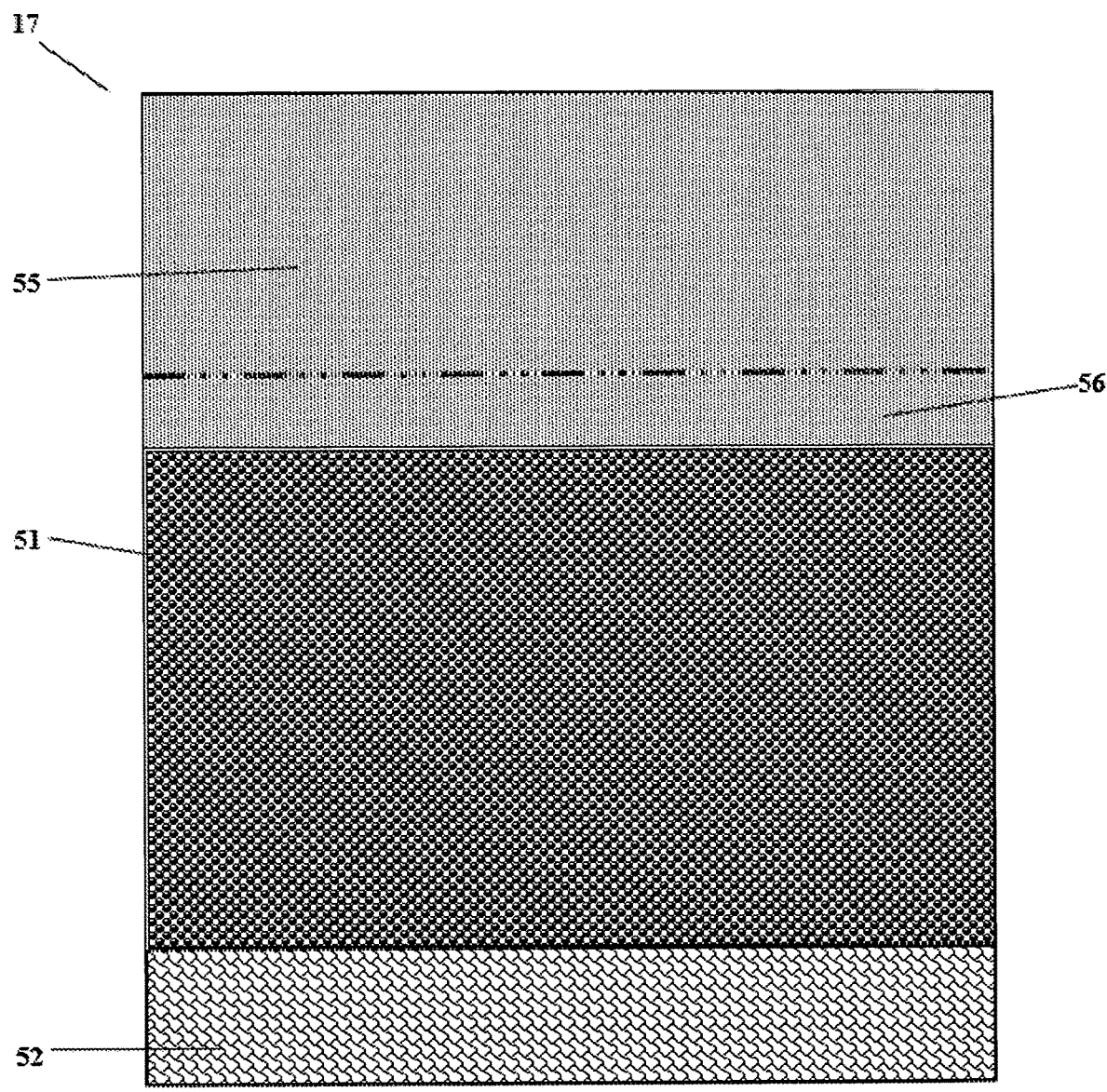
Figure 2E:
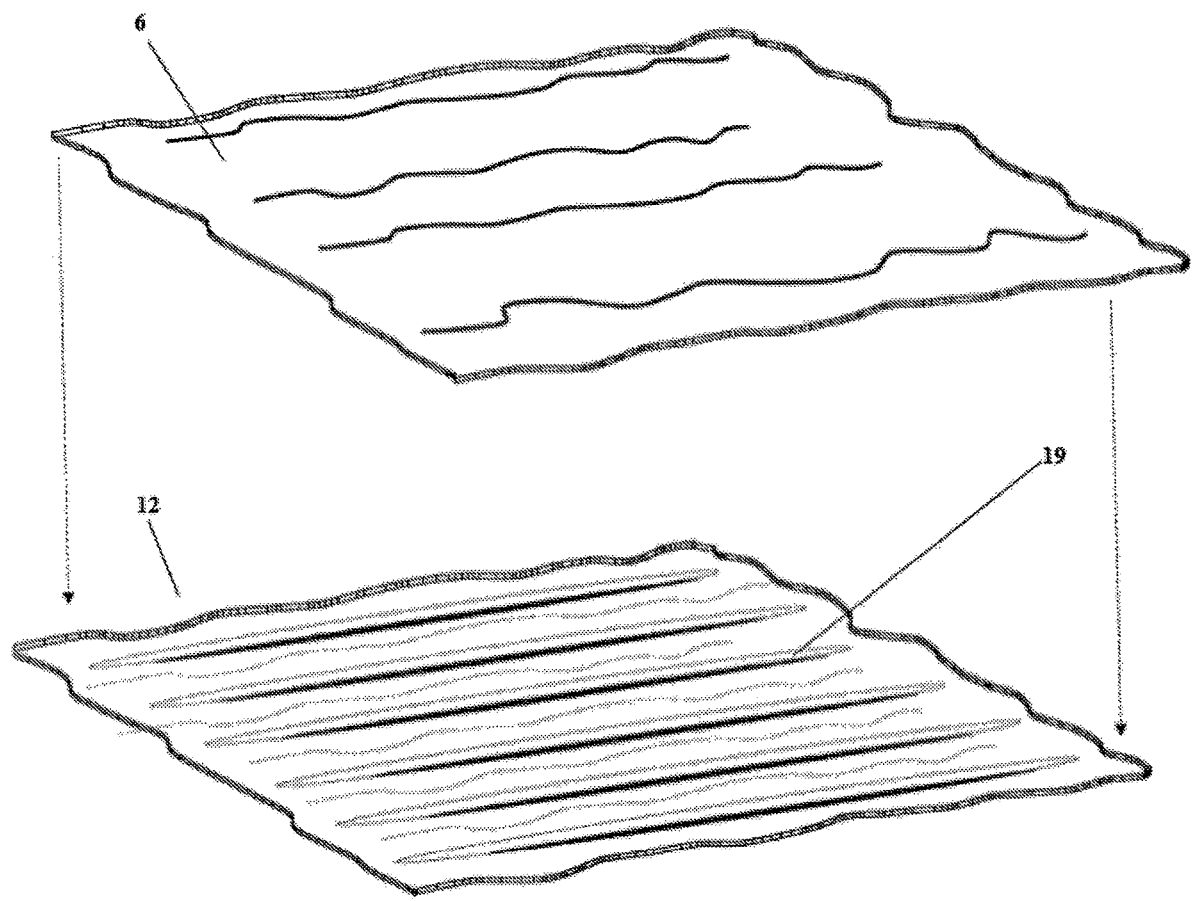

Further, the first absorbent channel layer 12 absorbent channels 17 component capacity ratio is approximately 10% of loose absorbent fibrous matrix of cotton fluff pulp 52, the super absorbent pods 51 covers approximately 50% capacity (space) of the absorbent channels 17, further the super absorbent pods 51 is respectively impregnated with super absorbent polymer (SAP) 53 in the form of fine particles of sodium polyacrylate at 75% and hydrophilic polymer at 25%, and approximately 40% of loose fine particles of super absorbent polymer (SAP) in the form of sodium polyacrylate 55 at 75% and hydrophilic polymer 56 at 25% FIG. 2D.

The super absorbent pods 51 impregnated into the first absorbent channel layer 12 absorbent channels 17 are approximately 5 mm to 8 mm in overall spherical circumference, composing a 100% ratio of super absorbent polymer (SAP). The loose absorbent fibrous matrix, super absorbent pods 51, and loose fine particles of super absorbent polymer (SAP) may be dispersed through the first absorbent channels 17 at the time the first absorbent channel layer 12 is created, or by any means available to those skilled in the art(s). The rear-side of the first absorbent channel layer 12 composes channel openings 19 at regions where the absorbent channels 17 are formed. The complete rear-side of the first absorbent channel layer 12 is enclosed with a reedy permeable sheet 6 by a stitching, adhesive, or lamination method FIG. 2E. Further, when the first absorbent channel layer 12 is made of a foam-type material the overall region is covered with a reedy permeable sheet made of a super-absorbent material.

Figure 3A:
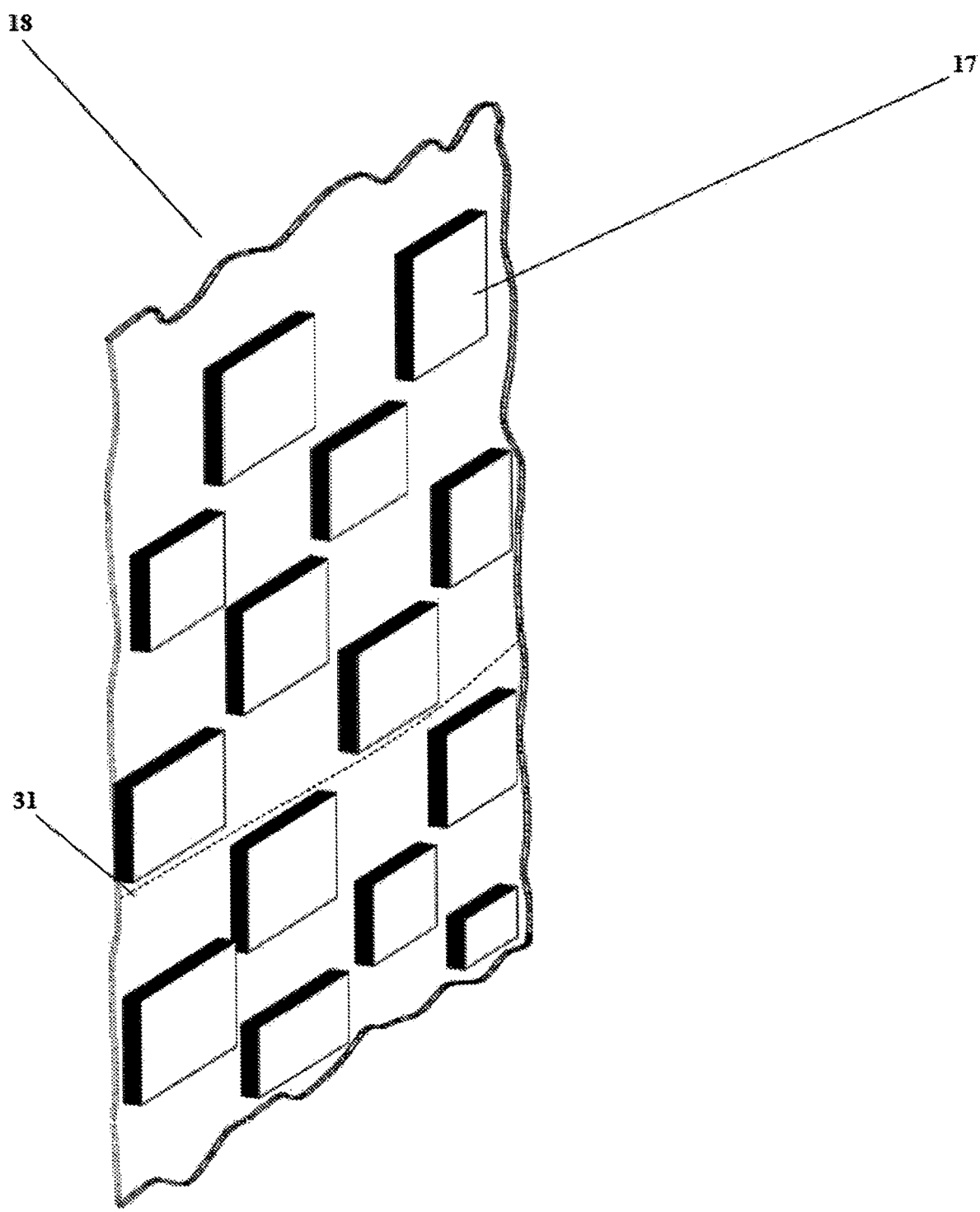
FIG. 3A-3C is a perspective view of an layer structuring of an potty/bed pan liner article according to one embodiment.
Figure 3B:
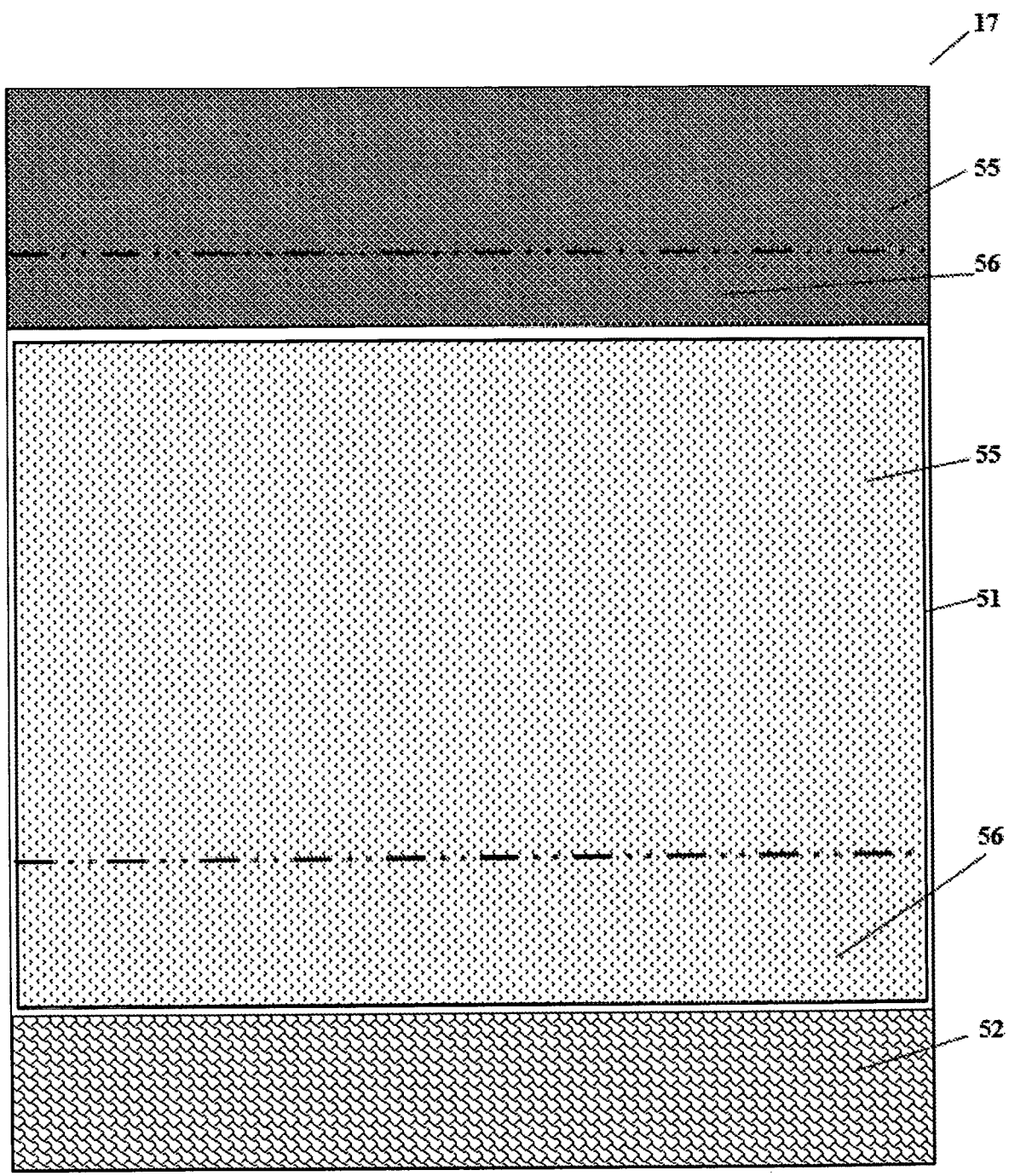

FIG. 3A-3B is a perspective view of the layer structuring of the liner 1. Additionally, the inner portion of the liner 1 composes an bowl shape intermediate absorbent channel layer 18 respectively coupled to the exterior of the first absorbent channel layer 12, where the top edges of the intermediate absorbent channel layer 18 overlaps the first absorbent channel layer 12 top edges thereon adjoining with the absorbent core 16 flange boarding 23 top edges. More of, the intermediate absorbent channel layer 18 composes a respectively dashed slit 31 arranged around it surface arranged at a circular (ring) direction approximately 38.1 mm to 76.2 mm above its base region, further the intermediate absorbent channel layer 18 dashed slit 31 arranges at a recessed region above or below at lease one absorbent channel 17, more of the dashed slit 31 respectively corresponds with the preceding first non-permeable layer 2 dashed slit 31, first absorbent channel layer 12 dashed slit 31, absorbent core 16 dashed slit 31, and top permeable layer 22 dashed slit 31 which allocates the entire lower region of the intermediate absorbent channel layer 18 below the dashed slit 31 to bifurcate with the preceding lower region of the first non-permeable layer 2, first absorbent channel layer 12, absorbent core 16 and top permeable layer 22.

Further, the intermediate absorbent channel layer 18 forms a reedy permeable sheet where numerous regions of its structure forms effervesce square-shape pockets that extends profusely in a direction away from the body of the absorbent channel layer 12 forming the absorbent channels 17 FIG. 3A. The absorbent channels 17 pattern covers a partial region of the absorbent channel layer 12.

However, the intermediate absorbent channel layer 18 absorbent channels 17 is impregnated with a combination of material capable of maintaining the shape and pattern structure of the absorbent channels 17 and converting the absorbent channels 17 regions from a dry permeable texture to a gel-like permeable texture when in contact with a liquid substance.

More specifically, the intermediate absorbent channel layer 18 absorbent channels 17 contains a combination of loose absorbent fibrous matrix of cotton fluff pulp dispersed respectively throughout the bottom region of the absorbent channels 17, a super absorbent pod respectively arranged above the loose absorbent fibrous matrix at each absorbent channel 17, and loose fine particles of super absorbent polymer (SAP) dispersed respectively above engulfing the super absorbent pods. The intermediate absorbent channel layer 18 absorbent channels 17 component capacity ratio is approximately 10% of loose absorbent fibrous matrix of cotton fluff pulp 52, each super absorbent pods 51 cover approximately 70% capacity (space) of the absorbent channels 17 and is respectively impregnated with fine particles of super absorbent polymer (SAP) in the form of sodium polyacrylate 55 at 75% and hydrophilic polymer 56 at 25%, and approximately 30% of loose fine particles of super absorbent polymer (SAP) 53 in the form of sodium polyacrylate 55 at 75% and hydrophilic polymer 56 at 25% FIG. 3B.

Each super absorbent pod 51 of the intermediate absorbent channel layer 18 absorbent channels 17 forms a quadrilateral-shape marginally smaller than the overall circumference of the interior of the absorbent channels 17, respectively corresponding with the couture of the interior region of the intermediate absorbent channel layer 18 absorbent channels 17, composing a 100% ratio of super absorbent polymer (SAP).

Figure 3C:
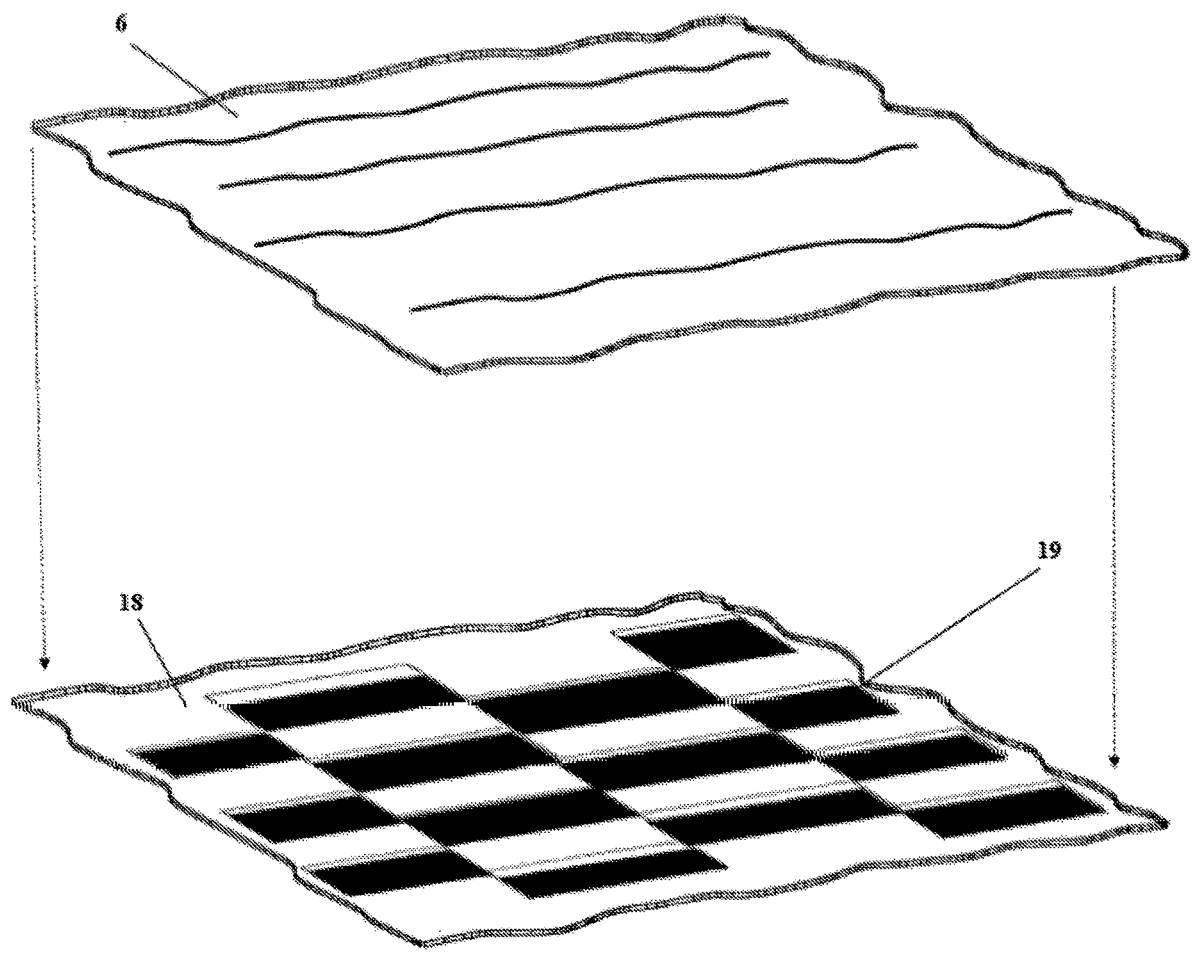

The rear-side of the intermediate absorbent channel layer 18 composes channel openings 19 at regions where the absorbent channels 17 are formed. The complete rear-side the of absorbent channel layer 12 is enclosed with an reedy permeable sheet 6 by an stitching, adhesive, or lamination method FIG. 3C.

The intermediate absorbent channel layer 18 is made of an low density foam, absorbent, or superabsorbent type material. Further, when the intermediate absorbent channel layer 18 is made of an micro-foam material the overall region is covered with an reedy preamble sheet made of an superabsorbent material.

Figure 4A:
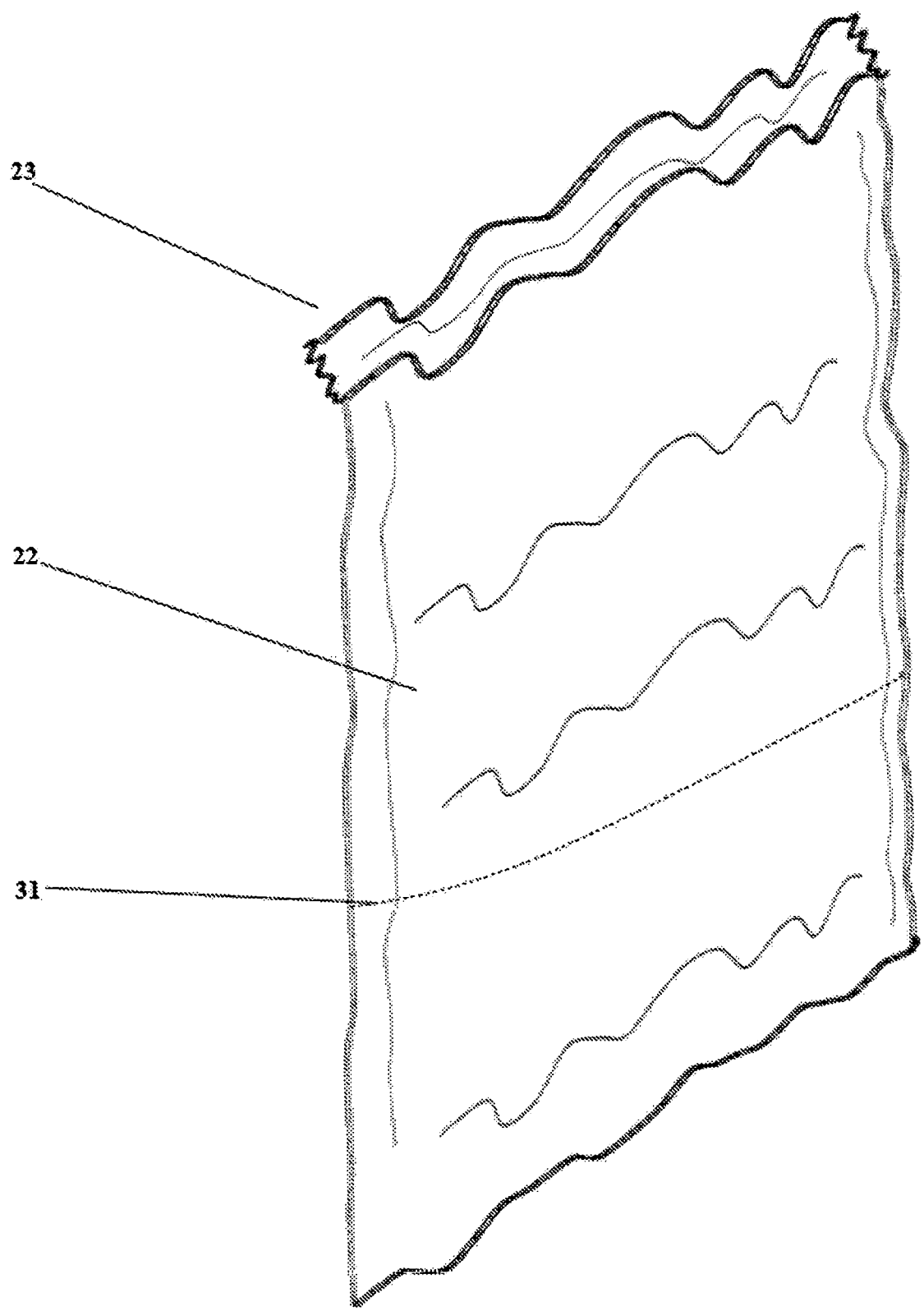
FIG. 4A-4B is a perspective view of an layer structuring of an potty/bed pan liner article according to one embodiment.
Figure 4B:
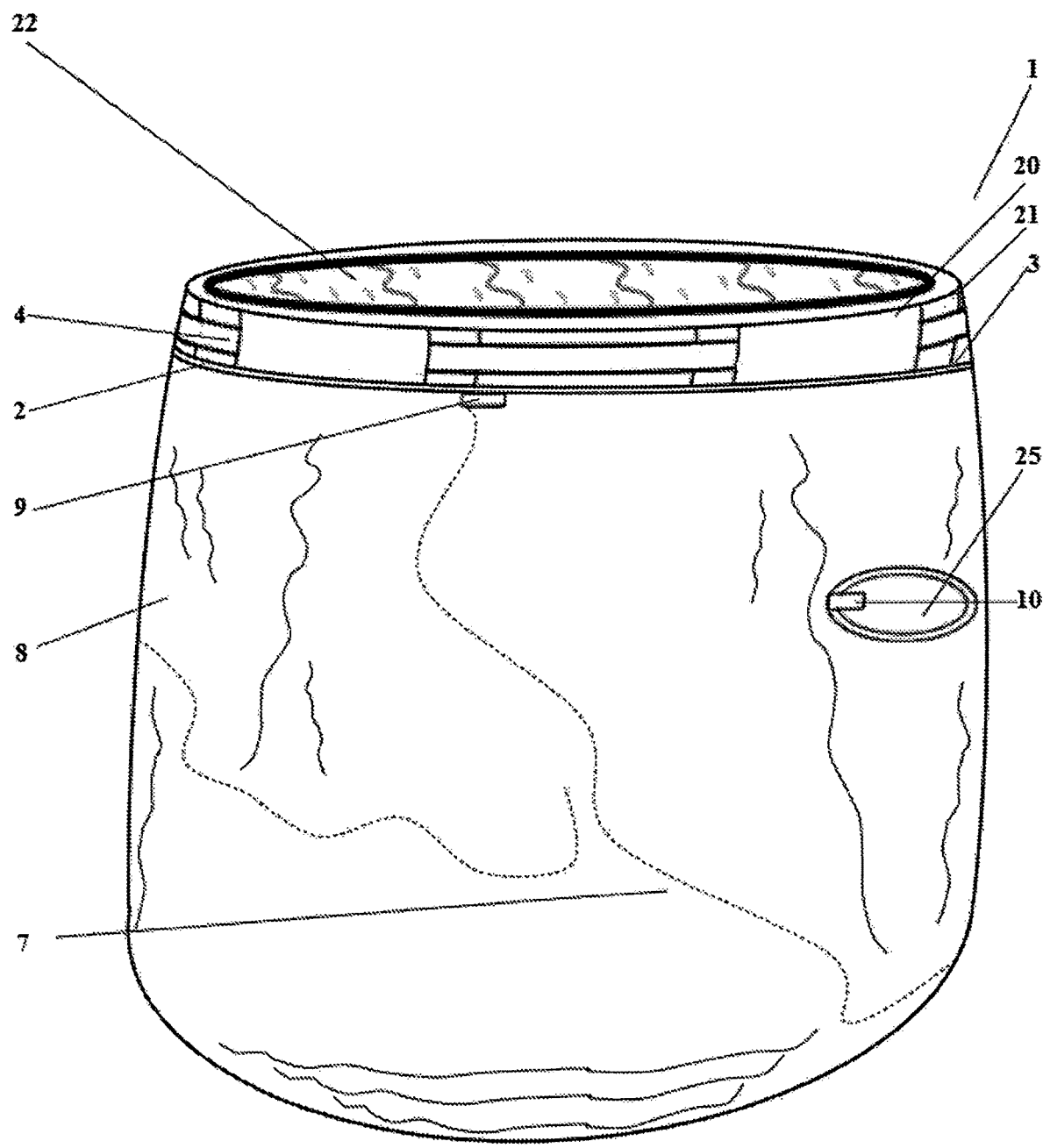

FIG. 4A-4B is a perspective view of the liner 1 in conjunction with the top permeable layer 22. The liner 1 composes an bowl shape top permeable layer 22 coupled to the exterior of the intermediate absorbent channel layer 18, where the top edges of the top permeable layer 22 flange boarding 23 symmetrically assembles with the intermediate absorbent channel layer 18 top edges and absorbent core 16 flange boarding 23 top edges thereon adjoining the top permeable layer 22 to the interior of the liner 1. The top permeable layer 22 forms the body of an reedy preamble sheet made of an superabsorbent material. The top permeable layer 22 arranges a extending portion that completely boarders the top edges of top permeable layer 22 extending upwardly in direction approximately 12.07 mm to 25.04 mm in length forming the flange bordering 23. The top permeable layer 22 composes a respectively dashed slit 31 arranged around it surface arranged at a circular (ring) direction approximately 38.1 mm to 76.2 mm above its base, further the top permeable layer 22 dashed slit 31 respectively corresponds with the preceding first non-permeable layer 2 dashed slit 31, first absorbent channel layer 12 dashed slit 31, intermediate absorbent channel layer 18 dashed slit 31 and absorbent core 16 dashed slit 31 which allocates the entire lower region of the top permeable layer 22 below the dashed slit 31 to bifurcate with the preceding lower region of the first non-permeable layer 2, first absorbent channel layer 12, intermediate absorbent channel layer 18 and absorbent core 16 FIG. 4B.

FIG. 5A-5D is a perspective view of an layering structure of an child/adult diaper or child/adult training pants type absorbent article 40. Further, the absorbent article 40 composes any desired shape, such as rectangular, I-shaped, a hourglass shape, or a T-shape.

More of, the absorbent article 40 composes joining mechanisms at an beyond region of the said absorbent article 40 body composing fastener tabs 41 arranged at the back ears of the back waistband region and docking patches 42 arranged at the front ears of the front waistband region so that when both fastener tabs 41 convene with the docking patches 42 the absorbent article 40 arranges an firm fitting on the user. The docking patches 42 arranges an respectively target region for releasable and re-attachable securement in conjunction with the fastener tabs 41. Further, the docking patches 42 and fastener tabs 41 can be made of an substantially non-elastomeric material such as polymer films or tapes. The joining mechanisms may be of the hook-and loop type, velcro type or the fastener tab 41 can composes an sticky surface that respectively joins with the docking patches 42.

The absorbent article 40 normally composes an plurality of elastomeric gathering members, leg elastics 44 arranged to support the diaper firmly around the legs of an user, an waist elastic 45 to perpetually draw the diaper around the waist of an user, an plurality of repression flaps 54 arranged laterally adjacent inward from the leg elastics 44, and significantly symmetrically arranged on opposing sides of the longitudinal centerline of the absorbent article 40.

Alternatively, the absorbent article 40 may compose of additional elastomeric gathering member at specific regions of its body known to one skilled in the art(s).

Further, the absorbent article 40 composes an rectangular-shaped, I-shaped, hourglass shape, or T-shaped non-permeable body/outer core 46 made up of an conjunction of breathable polyethylene or nonwoven microlayer films and fiber composite forming the overall foundation of the said absorbent article 40 which traditionally supports the preceding interior permeable layers and may contain many other components respectively affixed thereon.

The absorbent article 40 composes an rectangular-shaped, I-shaped, hourglass shape, or T-shaped absorbent core 16 that respectively corresponds with the couture of the interior of the non-permeable body/outer core 46 affixed to the interior of the non-permeable body/outer core 46, forming the body of an sack/pouch, comprising an extending portion that completely boarders the top, bottom and side edges of the sack/pouch portion 24 partially extending outwardly in direction away from the sack/pouch portion 24 forming an flange bordering 23, where the absorbent core 16 flanged boarding 23 outer edges 48 is respectively affixed at the interior edges of the non-permeable body/outer core 46. Specifically, the flanged boarding 23 extend approximately 6.35 mm to 25.04 mm in length away from the body of the absorbent core 16.

The absorbent core 16 sack/pouch portion 24 is impregnated with a combination of loose absorbent fibrous matrix, a plurality of super absorbent pods impregnated with loose fine particles of super absorbent polymer (SAP), and loose fine particles of super absorbent polymer (SAP) capable of converting the absorbent core 16 region from a dry permeable texture to a moist gel-like permeable texture when in contact with an liquid substance.

More specifically, the absorbent core 16 sack/pouch portion 24 is impregnated with a combination of a loose absorbent fibrous matrix of cotton fluff pulp dispersed respectively throughout the bottom region of the absorbent core 16 sack/pouch portion 24, a plurality of super absorbent pods dispersed respectively above the loose absorbent fibrous matrix, and loose fine particles of super absorbent polymer (SAP) dispersed respectively above engulfing the super absorbent pods.

Figure 5A:
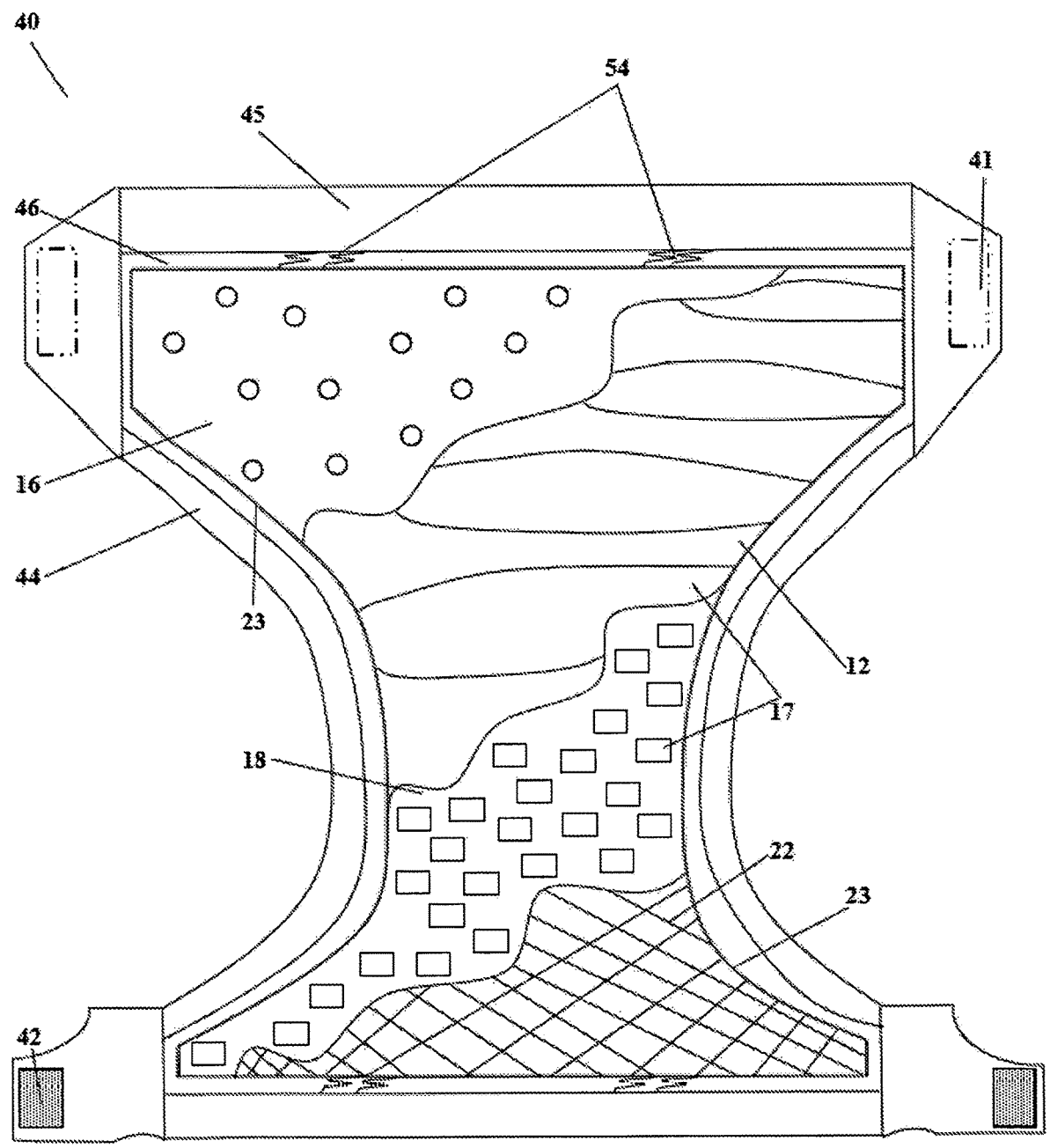
FIG. 5A-5D is a perspective view of an layer structuring of an child/adult diaper, or feminine liner article according to one embodiment.
Figure 5B:
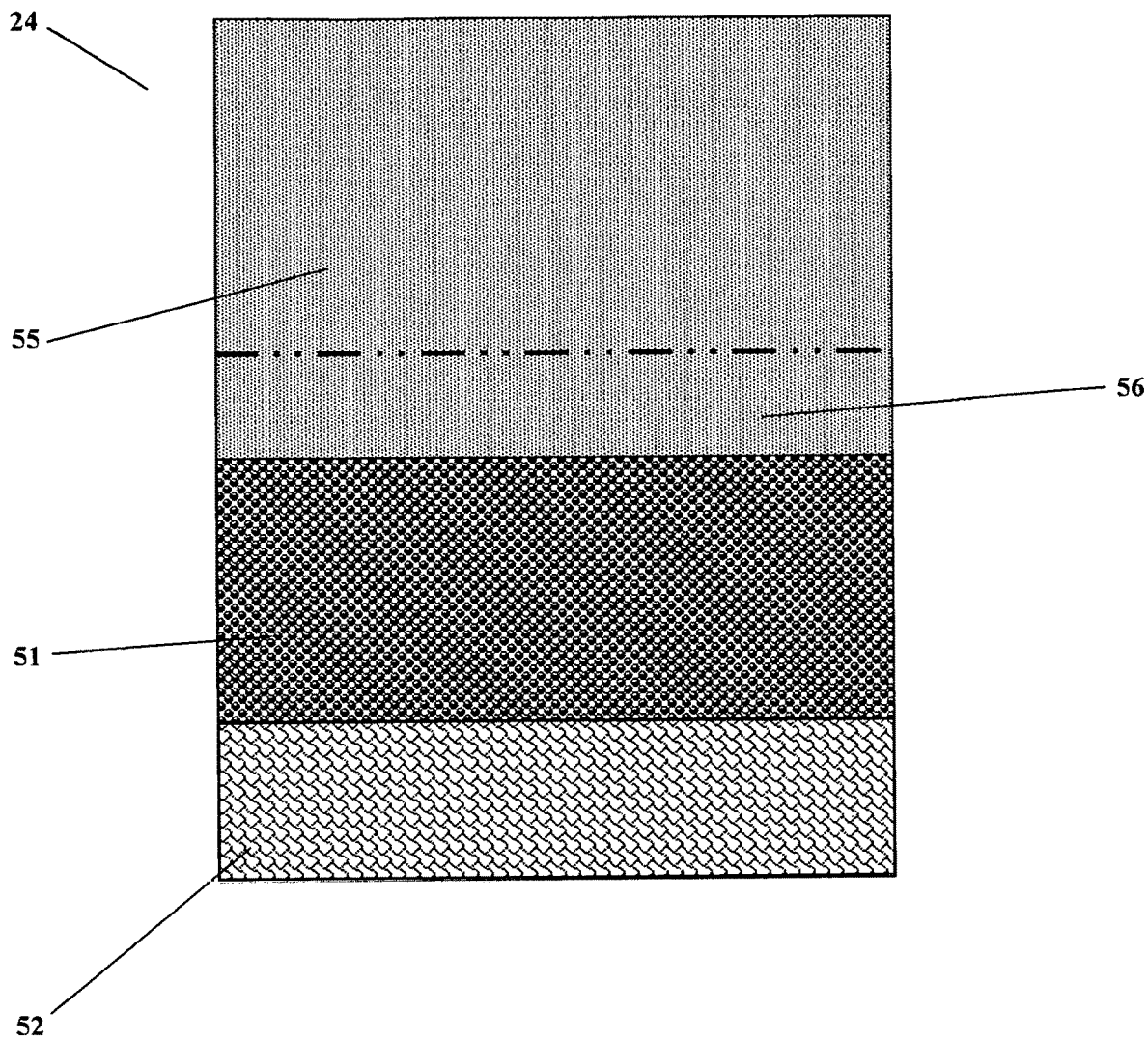

The absorbent core 16 sack/pouch portion 24 component capacity ratio is approximately 10% to 20% of loose absorbent fibrous matrix 52 of cotton fluff pulp, approximately 20% to 30% of super absorbent pods 51, further the super absorbent pods 51 are impregnated with super absorbent polymer (SAP) in the form of fine particles of sodium polyacrylate at 75% and hydrophilic polymer at 25%, and approximately 40% to 60% of loose fine particles of super absorbent polymer (SAP) 53 in the form of fine particles of sodium polyacrylate 55 at 75% and hydrophilic polymer 56 at 25% FIG. 5B.

The super absorbent pods impregnated into the absorbent core 16 sack/pouch portion 24 forms a flat elliptical-shape approximately 3 mm to 7 mm in overall elliptical circumference, composing a 100% ratio of super absorbent polymer (SAP). In conjunction, the interior walls of the sack/pouch portion 24 composes a light coating of adhesive to retain a perpetual amount of absorbent fibrous matrix and loose fine particles of super absorbent polymer (SAP) in place and to ensure evenly distribution of coverage.

Furthermore, the inner region of the absorbent article 40 composes an rectangular-shaped, I-shaped, hourglass shape, or T-shaped first absorbent channel layer 12 that respectively corresponds with the couture of the interior of the non-permeable body/outer core 46 respectively coupled to the exterior of the absorbent core 16, where the top, bottom and side outer edges 47 of the first absorbent channel layer 12 overlaps the absorbent core 16 flange boarding 23 arranging approximately 3.02 mm to 12.52 mm inward adjacent the absorbent core 16 flange boarding 23 outer edges 47 thereon adjoining the first absorbent channel layer 12 to the absorbent core 16.

The first absorbent channel layer 12 forms a reedy permeable sheet where numerous regions of the structure forms effervesce circular shaped pockets that extends profusely in a direction away from body of first absorbent channel layer 12 forming the absorbent channels 17, whereas the regions in-between the absorbent channels 17 arranges at a profoundly recessed structure. Further, the absorbent channels 17 respectively arranges at a horizontal direction approximately 12.07 mm to 25.04 mm apart from each-other. Further, the absorbent channels 17 pattern covers the entire region of the first absorbent channel layer 12 whereas the opposing non-absorbent channel regions are profoundly recessed.

Additionally, the rear-side of the first absorbent channel layer 12 composes respectively channel openings 19 at regions where the absorbent channels 12 are formed, the channel opening 19 is impregnated with a combination of materials capable of maintaining the shape and pattern structure of the absorbent channels 17 and converting the absorbent channels 17 from a dry permeable texture to a gel-like permeable texture when in contact with a liquid substance.

Precisely, the absorbent article 40 absorbent channels 17 contains a combination of loose absorbent fibrous matrix dispersed respectively throughout the bottom of the channel openings 19, a super absorbent pod arranged above the loose absorbent fibrous matrix at each absorbent channel 17, and loose fine particles of super absorbent polymer (SAP) dispersed respectively above engulfing the super absorbent pods at each absorbent channel 17.

Figure 5C:
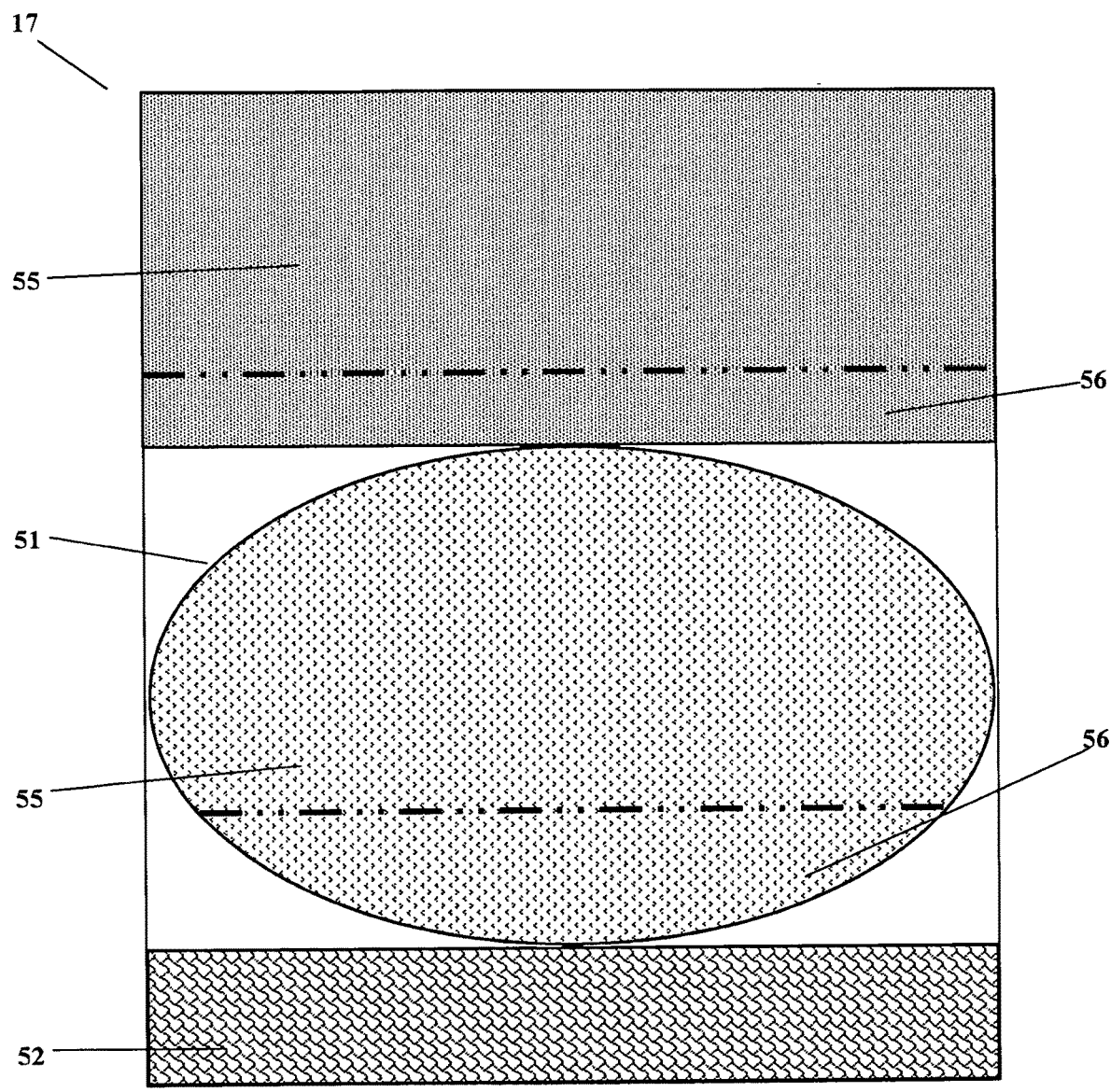
Figure 5D:
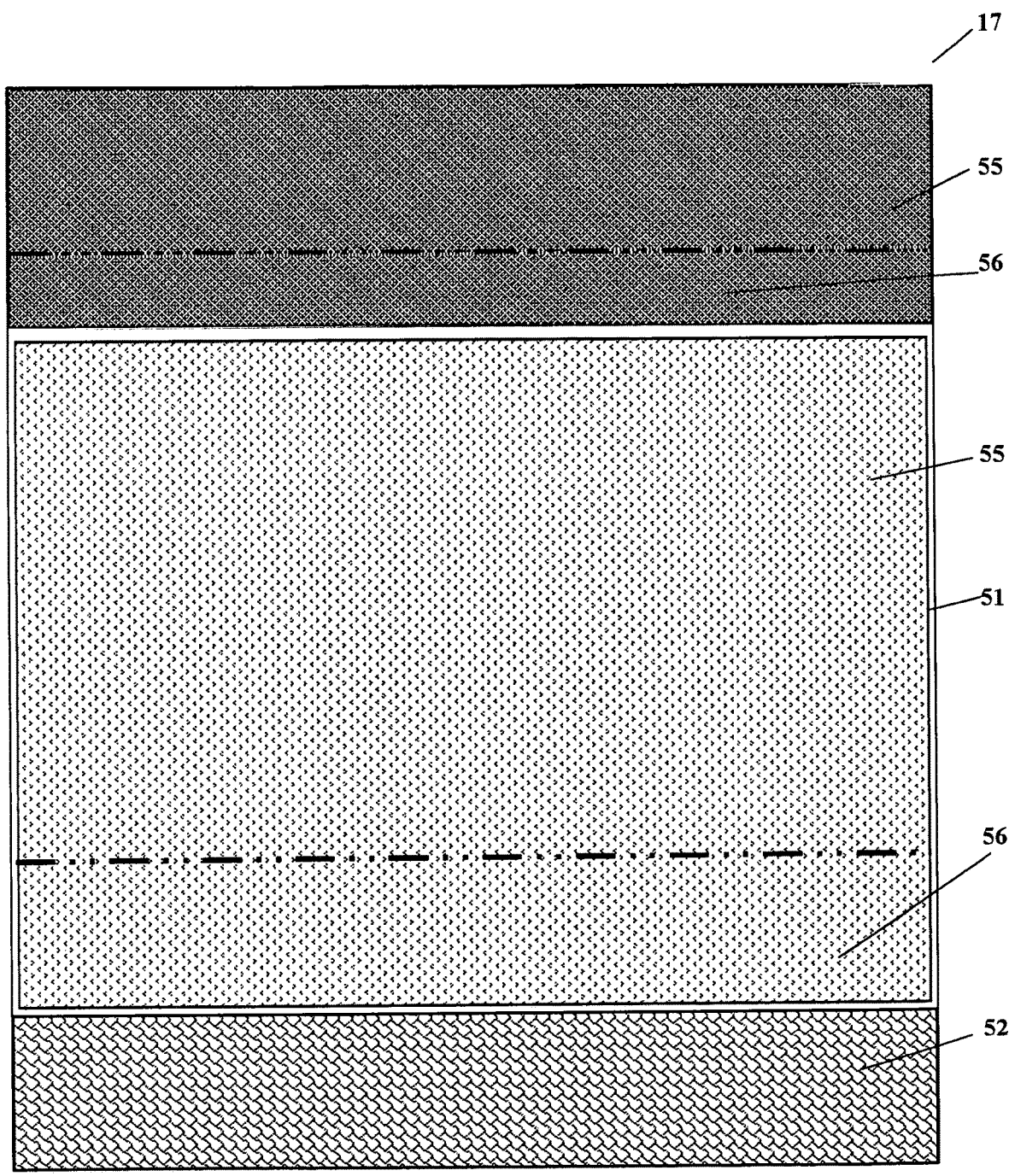

Further, the first absorbent channel layer 12 absorbent channels 17 component capacity ratio is approximately 10% of loose absorbent fibrous matrix of cotton fluff pulp 52, each super absorbent pods 51 covers approximately 50% capacity (space) of the absorbent channels 17 and is respectively impregnated with fine particles of super absorbent polymer (SAP) in the form of sodium polyacrylate 55 at 75% and hydrophilic polymer 56 at 25%, and approximately 40% of loose fine particles of super absorbent polymer (SAP) in the form of sodium polyacrylate 55 at 75% and hydrophilic polymer 56 at 25% FIG. 5C. Each super absorbent pod of the first absorbent channel layer 12 absorbent channels 17 forms a protruding elliptical-shape, respectively corresponding with the couture of the first absorbent channel layer 12 absorbent channels 17, composing a 100% ratio of super absorbent polymer (SAP). More of, the interior walls of the first absorbent channel layer 12 absorbent channels 17 composes an light coating of adhesive to retain a perpetual amount of absorbent fibrous matrix and loose fine particles of super absorbent polymer (SAP) in place and to ensure evenly distribution of coverage.

The complete rear-side of the first absorbent channel layer 12 is enclosed with an reedy permeable sheet 6 by an stitching, adhesive or lamination method. Alternatively, when first the absorbent channel layer 12 is made of an micro-foam material the overall region is covered with an reedy permeable sheet made of an superabsorbent material.

Additionally, the absorbent article 40 composes an rectangular-shaped, I-shaped, hourglass shape, or T-shaped intermediate absorbent channel layer 18 coupled to the exterior of the first absorbent channel layer 12, where the top, bottom and side outer edges 50 of the intermediate absorbent channel layer 18 respectively overlaps the first absorbent channel layer 12 outer edges 47 thereon respectively symmetrically adjoining with the absorbent core 16 flange boarding 23 outer edges 48.

Further, the intermediate absorbent channel layer 18 forms a reedy permeable sheet where numerous regions of the structure forms effervesce square-shape pockets that extends profusely in a direction away from the body of the intermediate absorbent channel layer 18 forming the absorbent channels 17, whereas in-between the absorbent channels 12 arranges a profoundly recessed structure. Further, the absorbent channels 17 pattern covers the entire region of the absorbent channel layer 12. However, the rear-side the of intermediate absorbent channel layer 18 composes respectively channel openings 19 where the absorbent channels 12 are formed, additionally the channel opening 19 is impregnated with a combination of material capable of maintaining the shape and pattern structure of the absorbent channels 17 and converting the absorbent channels 17 from a dry permeable texture to a gel-like permeable texture when in contact with a liquid substance.

The intermediate absorbent channel layer 18 absorbent channels 17 contains a combination of loose absorbent fibrous matrix dispersed respectively throughout the bottom of the absorbent channels 17, a super absorbent pod respectively arranged above the loose absorbent fibrous matrix at each absorbent channel 17, and loose fine particles of super absorbent polymer (SAP) dispersed respectively above engulfing the super absorbent pods. Further, the intermediate absorbent channel layer 18 absorbent channels 17 component capacity ratio is approximately 10% of loose absorbent fibrous matrix of cotton fluff pulp 52, each super absorbent pods 51 covers approximately 50% capacity (space) of the absorbent channels 17 and is respectively impregnated with fine particles of super absorbent polymer (SAP) in the form of sodium polyacrylate 55 at 75% and hydrophilic polymer 56 at 25%, and approximately 40% of loose fine particles of super absorbent polymer (SAP) in the form of sodium polyacrylate 55 at 75% and hydrophilic polymer 56 at 25% FIG. 5D.

Further, each super absorbent pod of the intermediate absorbent channel layer 18 absorbent channels 17 forms a quadrilateral-shape marginally smaller than the overall circumference of the interior of the absorbent channels 17, respectively corresponding with the couture of the interior of the intermediate absorbent channel layer 18 absorbent channels 17, composing a 100% ratio of super absorbent polymer (SAP). Additionally, the interior walls of the intermediate absorbent channel layer 18 absorbent channels 17 composes a light coating of adhesive to retain a perpetual amount of absorbent fibrous matrix and fine particles of super absorbent polymer (SAP) in place and to ensure evenly distribution of coverage.

The complete rear-side of the intermediate absorbent channel layer 18 absorbent channel layer 12 is enclosed with a reedy permeable sheet 6 by stitching or adhesive.

Further, when the intermediate absorbent channel layer 18 is made of an micro-foam material the overall region is covered with an reedy permeable sheet made of an super-absorbent material.

In addition, the absorbent article 40 composes an rectangular-shaped, I-shaped, hourglass shape, or T-shaped top permeable layer 22 coupled to the exterior of the intermediate absorbent channel layer 18, forming the body of an reedy permeable sheet, comprising an extending portion that completely boarders the top, bottom and side edges of the top permeable layer 22 extending away from the body in direction, where the outer edges 49 of the top permeable layer 22 flange boarding 23 respectively symmetrically assembles with the intermediate absorbent channel layer 18 outer edges 50 and absorbent core 16 flange boarding 23 outer edges 47 thereon respectively adjoining the top permeable layer 22 to the interior of the absorbent article 40. The top permeable layer 22 extending portion extends approximately 6.35 mm to 12.07 mm in length forming the flange bordering 23. In due process the affixing of the layering structuring to an adjacent layer of the absorbent article 40 can be the likes of an stitching, adhesive, or lamination joining method known to one skilled in the art(s).

The present invention may compose multi-microlayer films composed of an assembly of coextruded microlayers of thermoplastic elastomers and polymers. Specifically, the component "Multi-microlayer" refers to an film having a plurality of alternating microlayers wherein, based upon the process at which the film is formed, where each microlayer becomes partially integrated or adhered with the microlayers arranged above and below the microlayer.

Additionally, during formation of the films, which may include stretching, the microlayers will partially delaminate from one another, thereby permitting the corrugations to be formed upon relaxation or activation of the film. However, partial integration or adherence of microlayers remains, unlike certain prior multi-layer films. The system of this invention includes a plurality of corrugated microlayered films, which may be corrugated in a machine direction and/or a cross-direction to form micro channel spaces. Alternatively, some or all of the microlayers may be biodegradable. The microlayered films may contain particulate filler material, which upon stretching of the film may provide porosity initiating sites.

For example, an method for making the microlayer films of the present invention is a microlayer coextrusion process wherein two or more polymers (e.g., polypropylene for the extensible microlayer and polyurethane for the elastomeric microlayer) are coextruded to form a laminate unit with two or more microlayers, which laminate unit can then be manipulated to multiply the number of layers in the film.

In conclusion, the first absorbent channel layer 12 and intermediate absorbent channel layer 18 design configural retains and absorbs liquid substances penetrated through one or more preceding layers at an quicker stage and reduces liquid substance that's predominately directed to the absorbent core 16 whereas an user gets more durability from an single usage of each absorbent article 40 and liner 1.

Although the preceding description contains significant detail, it should not be construed as limiting the scope of the invention but rather as providing illustrations of the preferred embodiment(s) of the invention.

Having described my invention, I claim:
1. An absorbent article comprising:
   a first non-permeable layer having an elastic placement portion;
   a second non-permeable layer;
   an elastic material disposed within said elastic placement portion comprising one or more components;
   a dashed swirled slit formed on said second non-permeable layer configured to allocate a user to bifurcate said second non-permeable layer from first non-permeable layer in response to the user pulling a tab a predetermine direction;

an adhesive tab affixed to said second non-permeable layer;

the article having a first portion formed of a material;

the article having a second portion formed of a material different than said first portion; said second portion comprises an adhesive strip disposed on a surface for coupling to said first portion;

wherein the first non-permeable layer composes a respective dashed slit formed around a surface arranged at a circular direction approximately 38.1 mm to 76.2 mm above a base region of the first non-permeable layer, whereas the dashed slit respectively corresponds with a dash slit of an absorbent core, a dash slit of a first absorbent channel layer, a dash slit of a intermediate absorbent channel layer, and a dash slit of a top permeable layer dashed lit which is configured to allocate the user to bifurcate an entire lower region of the first non-permeable layer, the absorbent core, the first absorbent channel layer, the intermediate absorbent channel layer and the top permeable layer below the respective dashed slit to form the first portion and second portion;

wherein the elastic material is introduced into the slits, wherein the elastic material is introduced into the slits of said elastic placement portion by a weaving process by a weaving process, and wherein a region of the elastic material are subjected outside of the elastic placement portion in-between every other said slit of said elastic placement portion;

wherein the absorbent core composes the respective dashed slit arranged around a surface arranged in a circular direction approximately 38.1 mm to 76.2 mm above a base of the absorbent core, wherein the dash slit of the absorbent core dashed corresponds with the dashed slit of the first non-permeable layer, the dash slit of the first absorbent channel layer, the dash slit of the intermediate absorbent channel layer and the dash slit of the top permeable layer which is configured to allocate the entire lower region of the absorbent core below the dashed slit to bifurcate with a preceding region of said first non-permeable layer, the first absorbent channel layer, the intermediate absorbent channel layer and the top permeable layer;

wherein the absorbent core is impregnated with a combination of a loose absorbent fibrous matrix, a plurality of super absorbent pods impregnated with loose fine particles of super absorbent polymer (SAP), and loose fine particles of super absorbent polymer (SAP) capable of converting the absorbent core from a dry permeable texture to a moist gel-like permeable texture when in contact with a liquid substance;

wherein the absorbent core contains the combination of loose absorbent fibrous matrix dispersed respectively throughout a bottom of a sack/pouch portion of the absorbent core, the plurality of super absorbent pods dispersed respectively above the loose absorbent fibrous matrix, and the loose fine particles of super absorbent polymer (SAP) dispersed respectively above and engulfing the super absorbent pods;

wherein the sack/pouch portion of the absorbent core comprises a component capacity ratio, wherein the component capacity ratio of the sack/pouch portion of the absorbent core is approximately 10% to 20% of the loose absorbent fibrous matrix which includes cotton fluff pulp, approximately 20% to 30% of the super absorbent pods, wherein the super absorbent pods are respectively impregnated with super absorbent polymer (SAP) in the form of fine particles of sodium polyacrylate at 75% and hydrophilic polymer at 25%, and approximately 40% to 60% of the loose fine particles of super absorbent polymer (SAP) in the form of fine particles of sodium polyacrylate at 75% and hydrophilic polymer at 25%;

wherein each of the super absorbent pods impregnated into the sack/pouch portion of the absorbent core is approximately 5 mm to 8 mm in overall spherical circumference;

wherein the dash slit of the first absorbent channel layer is arranged around a surface arranged at a circular direction approximately 38.1 mm to 76.2 mm above a base region of the first absorbent channel layer, wherein the dashed slit of the first absorbent channel layer is arranged at a recessed region above or below at lease one absorbent channel, the dashed slit respectively corresponds with the dashed slit of the first non-permeable layer, the dashed slit of the absorbent core, the dashed slit of the intermediate absorbent channel layer dashed slit, and the dashed slit of the top permeable layer which is configured to allocate the entire lower region of the first absorbent channel layer below the dashed slit to bifurcate with the preceding lower region of the first non-permeable layer, the absorbent core, intermediate absorbent channel layer and the top permeable layer, wherein the first absorbent channel layer forms a reedy permeable sheet where numerous regions of a structure forms effervesce circular shaped pockets that extends profusely in a direction away from a body of the first absorbent channel layer, and wherein the absorbent channels of the at least one absorbent channel direct around the absorbent channel layer at a horizontal ring direction approximately 12.07 mm to 25.04 mm apart from each-other, wherein channel openings of the channels of the first absorbent channel layer are impregnated with a combination of materials capable of maintaining a shape and pattern structure for converting the absorbent channels from a dry permeable texture to a gel-like permeable texture when in contact with a liquid substance; wherein the combination of materials of the channel of the first absorbent channel layer contains a combination of loose absorbent fibrous matrix dispersed respectively throughout a bottom of the channel openings, super absorbent pods respectively arranged above the loose absorbent fibrous matrix at each absorbent channel, and loose fine particles of super absorbent polymer (SAP) dispersed respectively above and engulfing the super absorbent pods;

wherein the channels of the first absorbent channel layer comprises a component capacity ratio, wherein the component capacity ratio of the first absorbent channel layer is approximately 10% of the loose absorbent fibrous matrix which includes cotton fluff pulp, the super absorbent pods covers approximately 50% capacity of the absorbent channels, the super absorbent pods is respectively impregnated with super absorbent polymer (SAP) in the form of fine particles of sodium polyacrylate at 75% and hydrophilic polymer at 25%, and approximately 40% of the loose fine particles of super absorbent polymer (SAP) in the form of sodium polyacrylate at 75% and hydrophilic polymer at 25%;

wherein each of the super absorbent pods impregnated into the channels of the first absorbent channel layer are approximately 5 mm to 8 mm in overall spherical circumference;

wherein the dashed slit of the intermediate absorbent channel layer is arranged around a surface arranged at a circular direction approximately 38.1 mm to 76.2 mm above a base of the intermediate absorbent channel layer, the dashed slit of the intermediate absorbent channel layer is arranged at a recess above or below at lease one absorbent channel, the dashed slit respectively corresponds with the first non-permeable layer, the first absorbent channel layer, the absorbent core dashed slit, and the top permeable layer dashed slit which is configured to allocate the entire lower region of the intermediate absorbent channel layer below the dashed slit to bifurcate with the region of the first non-permeable layer, the first absorbent channel layer, the absorbent core and the top permeable layer;

wherein the intermediate absorbent channel layer forms a reedy permeable sheet where numerous regions of a structure forms effervesce square-shape pockets that extends profusely in a direction away from a body of the intermediate absorbent channel layer;

wherein absorbent channel of the at least one absorbent channels of the intermediate absorbent channel layer are impregnated with a combination of materials capable of maintaining a shape and pattern structure of the absorbent channels and converting the absorbent channels from a dry permeable texture to a gel-like permeable texture when in contact with a liquid substance; and wherein the combination of materials of the channels of the intermediate absorbent channel layer absorbent channels contains a combination of loose absorbent fibrous matrix of cotton fluff pulp dispersed respectively throughout a bottom of the absorbent channels, a super absorbent pod respectively arranged above the loose absorbent fibrous matrix at each absorbent channel, and loose fine particles of super absorbent polymer (SAP) dispersed respectively above and engulfing the super absorbent pods;

wherein the channels of the intermediate absorbent channel layer comprises a component capacity ratio, wherein the component capacity ration of the intermediate absorbent channel layer is approximately 10% of the loose absorbent fibrous matrix of cotton fluff pulp, each super absorbent pods cover approximately 70% capacity of the absorbent channels and is respectively impregnated with fine particles of super absorbent polymer (SAP) in the form of sodium polyacrylate at 75% and hydrophilic polymer at 25%, and approximately 20% of the loose fine particles of super absorbent polymer (SAP) in the form of sodium polyacrylate at 75% and hydrophilic polymer at 25%;

wherein each super absorbent pod of the channels of the intermediate absorbent channel layer forms a quadrilateral-shape marginally smaller than an overall circumference of an interior of the absorbent channels, respectively corresponding with a couture of the interior of the absorbent channels; and wherein the dashed slit of the top permeable layer composes is arranged around a surface arranged at a circular direction approximately 38.1 mm to 76.2 mm above a base of the top permeable layer, the dashed slit of the top permeable layer respectively corresponds with the dashed slit of the first non-permeable layer, the dashed slit of the first absorbent channel layer, the dashed slit of the intermediate absorbent channel layer and the dashed slit of the absorbent core which is configured to allocate the entire lower region of the top permeable layer below the dashed slit to bifurcate with the preceding region of the first non-permeable layer, the first absorbent channel layer, the intermediate absorbent channel layer and the absorbent core.

2. The absorbent article of claim 1, wherein the plurality of slits of said elastic placement portion are approximately 38.1 mm to 63.05 apart from each other and approximately 12.07 mm to 19.05 mm in length vertically.

3. The absorbent article of claim 1, wherein the one or more components of said elastic material composes a respective button and a respective button hole.

4. The absorbent article of claim 1, wherein the one or more components of said elastic material composes a pair of hook(s) and a hook loop.

5. The absorbent article of claim 1, wherein the one or more components of said elastic material composes hook and loop material.

6. The absorbent article of claim 1, when said tab is configured to be pulled at a complete clock-wise or circular direction around said second non-permeable layer, whereby the entire said second non-permeable layer is bifurcated from said first non-permeable layer respectively.

7. The absorbent article of claim 1, whereas said tab is approximately 6.35 to 19.05 mm in longitude and approximately 6.35 mm to 12.07 mm in latitude according to dimensions.

8. The absorbent article of claim 1, whereas said adhesive tab is elliptical-shape.

9. The absorbent article of claim 1, further comprising said adhesive tab conceals a handle hole on said second non-permeable layer, whereas when said adhesive tab is removed from said second non-permeable layer this allocates a potty handle to deviate the hole from an interior of said second non-permeable layer.

10. The absorbent article of claim 1, whereas said first portion is made of an impermeable plastic material.

11. The absorbent article of claim 1, whereas said second portion composes the adhesive strip arranged around a top edge approximately 6.35 mm in width.

12. The absorbent article of claim 1, whereas said second portion is made of a liquid-soluble film made of a polyvinylalcohol (PVA) material.

13. The absorbent article of claim 1, farther comprising said second portion composes a dashed slit arranged at a circular direction approximately 6.35 mm below a joining region of said first portion and second portion.

14. The absorbent article of claim 1, further comprising said absorbent article is a liner.

15. The absorbent article of claim 1, further comprising said absorbent article comprises a rectangular shape, I-shape, hourglass shape, or T-shape.

* * * * *